(12) United States Patent
Fornell et al.

(10) Patent No.: US 11,633,154 B2
(45) Date of Patent: Apr. 25, 2023

(54) SYSTEM AND METHOD FOR MEASURING INFANT WEIGHT

(71) Applicant: HB Innovations, Inc., Los Angeles, CA (US)

(72) Inventors: Peter Fornell, Los Angeles, CA (US); Joseph J. Kopp, Jr., Los Angeles, CA (US); Kevin Bailey, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 447 days.

(21) Appl. No.: 17/006,223

(22) Filed: Aug. 28, 2020

(65) Prior Publication Data
US 2022/0061766 A1 Mar. 3, 2022

(51) Int. Cl.
| | |
|---|---|
| A61B 5/00 | (2006.01) |
| G01G 3/14 | (2006.01) |
| G01G 3/13 | (2006.01) |
| G01G 9/00 | (2006.01) |
| A61M 21/02 | (2006.01) |
| A61B 7/00 | (2006.01) |
| A61B 5/107 | (2006.01) |
| A61B 5/11 | (2006.01) |
| G16H 40/63 | (2018.01) |
| G16H 20/30 | (2018.01) |
| G01G 19/44 | (2006.01) |
| A61M 21/00 | (2006.01) |

(52) U.S. Cl.
CPC .......... *A61B 5/6892* (2013.01); *A61B 5/1072* (2013.01); *A61B 5/1115* (2013.01); *A61B 5/4818* (2013.01); *A61B 5/4866* (2013.01); *A61B 7/003* (2013.01); *A61M 21/02* (2013.01); *G01G 3/13* (2013.01); *G01G 3/14* (2013.01); *G01G 9/00* (2013.01); *G01G 19/445* (2013.01); *G16H 20/30* (2018.01); *G16H 40/63* (2018.01); *A61B 2503/04* (2013.01); *A61B 2562/0247* (2013.01); *A61B 2562/06* (2013.01); *A61M 2021/0022* (2013.01)

(58) Field of Classification Search
CPC .................. A47D 9/00; A61B 2503/04; A61B 2562/0247; A61B 2562/06; A61B 5/1072; A61B 5/1113; A61B 5/1115; A61B 5/113; A61B 5/4815; A61B 5/4818; A61B 5/4866; A61B 5/6892; A61B 7/003; A61M 2021/0022; A61M 21/02; G01G 19/445; G01G 3/13; G01G 3/14; G01G 9/00; G16H 20/30; G16H 40/63
See application file for complete search history.

(56) References Cited

U.S. PATENT DOCUMENTS

| | | |
|---|---|---|
| 4,750,474 A | 6/1988 | Dukhan et al. |
| 5,853,005 A | 12/1998 | Scanlon |
| 8,927,883 B2 | 1/2015 | Roth |

(Continued)

OTHER PUBLICATIONS

International Search Report and Written Opinion, PCT/US2021/029815, dated Aug. 5, 2021.

*Primary Examiner* — George Manuel
(74) *Attorney, Agent, or Firm* — Akerman LLP

(57) ABSTRACT

An infant sleep device may include a platform for supporting an infant, a base upon which the platform is supported, and one or more weight sensors positioned to measure weight of an infant positioned on the platform.

29 Claims, 25 Drawing Sheets

(56) References Cited

U.S. PATENT DOCUMENTS

| | | |
|---|---|---|
| 2014/0250592 A1 | 9/2014 | Karp et al. |
| 2016/0058361 A1 | 3/2016 | Melamed |
| 2016/0183861 A1* | 6/2016 | Hayes ................ A61B 5/02055 600/595 |
| 2017/0065102 A1 | 3/2017 | Liou |
| 2018/0325280 A1* | 11/2018 | Paperno ................... A61B 5/11 |
| 2019/0125215 A1 | 5/2019 | Swanson et al. |

* cited by examiner

SYSTEM AND METHOD FOR MEASURING INFANT WEIGHT

TECHNICAL FIELD

This disclosure generally relates to systems and methods for detecting and monitoring infant weight within a sleep device. In disclosed embodiments, systems and methods are described for collecting infant weight, filtering said data, and analyzing the same alone or together with additional infant data.

BACKGROUND

Infant weight is typically measured at birth and periodically thereafter during medical care visits. These weight measurements are used to track growth of the infant and are typically compared to standardized growth and weight charts. While there is significant variation in weight gain between individual infants, infants typically rapidly increase in weight. For example, an infant's weight may double by 3 to 4 months following birth.

SUMMARY

In various embodiments, a weight detection system is configured to measure weight of an infant when positioned on a platform of a sleep device. The weight detection system may be configured to utilize weight sensors such as load cells, strain gauges, or compression sensors below the platform to measure weight. The weight detection system may be configured to collect weight data for various applications. For example, weight may be collected for caregivers to help track weight changes over time. In some embodiments, the weight data may be analyzed to determine a feeding state. For example, weight data may be compared to previously collected weight data to determine if the infant is underfed, overfed, or properly fed and/or satiated. The analysis may consider other data collected such as sleep duration, sleep quality, or behavior state associated with previous weight measurements or may compare the weight data to a weight pattern, general or personalized weight profile, or threshold values. In an above or another example, weight data may be analyzed to better understand feeding patterns. For instance, infants may spend a majority of their time in a sleep device. Monitoring weight throughout the day may provide insight into feeding patterns and effects of such feeding. For example, feeding patterns may be correlated with sleep patterns for advising caregivers regarding feeding times and amounts. Monitoring weight may also be used as a health indicator and/or for early diagnosis of health issues, e.g., when rapid weight loss is observed. Weight may also be monitored as an indicator of motion. For example, weight sensors may be used to detect motion and wiggling of an infant in the sleep device. Utilizing signal processing and/or other ancillary information, the weight detection system may be utilized to determine if the infant is in distress. This may provide critical information to have to determine sudden infant death syndrome (SIDS). In an above or another example, using weight sensors as an indicator of motion may be used to assist in identification of restless sleeping patterns and/or as an indicator of other conditions. In various embodiments, the weight detection system is configured for use with a sleep device having a movable platform.

In one aspect, an infant sleep device includes a platform for supporting an infant, a base upon which the platform is supported, wherein the platform is configured to move above and relative to the base; and one or more weight sensors positioned to measure weight of an infant positioned on the platform.

In one example, one or more weight sensors may be positioned between the platform and the base. In a further example, the one or more weight sensors comprise one or more load cells.

In any of the above or another example, the sleep device may comprise a platform mount that mounts between the base and the platform and is configured to move above and relative to the base with the platform. The platform may couple to the platform mount. One or more weight sensors may be positioned between the platform mount and the platform.

In one example, the one or more weight sensors comprise load cells.

In any of the above or another example, one or more bearings may be positioned between the platform mount and the base. The platform mount may mount onto the bearing and be movable thereon over and relative to the base thereon. In one example, the sleep device may further comprise a drive system operable to drive the movement of the platform mount and coupled platform over and relative to base on the one or more bearings.

In any of the above or another example, the sleep device may include or integrate with a controller configured to calculate weight data generated or collected by the one or more weight sensors. The controller may include an analysis module configured to analyze the weight data.

In a further example, the analysis module may be configured to determine a feeding state of the infant, track weight of the infant over time, generate a weight profile, identify rapid weight gain or weight loss, identify abnormal weight change patterns, identify movements and restlessness of the infant, or combination thereof.

In the above or another example, the analysis module may be configured to track movements of infant on the platform and perform analysis to determine restlessness, irregular or periodic movement patterns or a distress condition such as choking or SUID.

In the above or another example, the analysis module may be configured to track presence of infant on the platform and transmit a notification to a user interface when the presence of the infant is not detected on the platform.

In any of the above or another example, the analysis module may be configured to compare collected weight data to previously collected weight data to determine if the infant is underfed, overfed, or properly fed and/or satiated.

In any of the above or another example, the controller may be configured to transmit collected weight data to a back-end system for analysis and/or historical storage, wherein the analysis of the weight data includes one or more of (a) identification of population trends and/or individual historical trends; (b) comparative analysis of weight data associated to an individual infant versus population; or (c) comparative analysis of the collected data associated with the infant versus population.

In still another aspect, a weight detection system for a sleep device includes a controller configured to receive weight data collected by one or more weight sensors positioned to detect a weight of an infant supported on a platform of a sleep device. The controller may include an analysis module configured to analyze the weight data collected by the one or more weight sensors.

In one example, the analysis module is configured to determine a feeding state of the infant, track weight of the infant over time, generate a weight profile, identify rapid weight gain or weight loss, identify abnormal weight change patterns, identify movements and restlessness of the infant, or combination thereof.

In the above or another example, wherein the analysis module may be configured to track changes in weight over time.

In any of the above or another example, the analysis module may be configured to track presence of an infant on the platform and to transmit a notification to a user interface when the presence of the infant is not detected on the platform.

In any of the above or another example, the analysis module may be configured to track duration of time the infant spends on the platform of the sleep device.

In any of the above or another example, the analysis module may be configured to identify feeding patterns and how the feeding patterns affect sleep timing, duration, or quality.

In any of the above or another example, the controller may be configured to transmit collected weight data to a back-end system for analysis and/or historical storage, wherein the analysis of the weight data includes one or more of (a) identification of population trends and/or individual historical trends; (b) comparative analysis of weight data associated to an individual infant versus population; or (c) comparative analysis of the collected data associated with the infant versus population.

In any of the above or another example, when the analysis module determines the infant is underfed, the controller may be configured to generate a notification to a user interface that infant is underfed.

In any of the above or another example, when the analysis module may be configured to generate a feeding schedule based on a desired or optimal sleep time, wherein the feeding schedule identifies a time range and amount of food the infant is to be fed within the time range prior to the desired or optimal sleep time. In a further example, the sleep time includes a sleep duration.

In any of the above or another example, the controller may be configured to receive data related to the infant from one or more additional sensors. The analysis module may be configured to analyze the data collected from the one or more additional sensors to determine a behavior state of the infant and correlate the behavior state to weight data collected proximate to the collection of the data collected from the one or more additional sensors to identify how weight patterns affect behavior state. In one example, the one or more additional sensors comprise one or more of motion sensors, sound sensors, breath sensors, biological sensors, or combination thereof. In another example, the additional sensor are microphone(s) to determine if a choking condition is occurring based on the combinatorial events of movement and sound.

In any of the above or another example, the controller may be configured to receive data from one or more additional sensors configured to collect length and/or circumference data with respect to the infant. In one example, the one or more additional sensors includes a pressure mat.

In any of the above or another example, the analysis module may be located in the cloud or other remote computing location.

In one aspect, an infant sleep device includes a platform for supporting an infant, a base upon which the platform is supported, and one or more weight sensors positioned to measure weight of an infant positioned on the platform.

In an example, the one or more weight sensors may be positioned between the platform and the base. The one or more weight sensors may include one or more load cells.

In an above or another example, the platform may be configured to rotate above the base. One or more bearings may be positioned between the platform and the base. The platform may rotate above the base on one or more bearings.

In any of the above or another example, the infant sleep device may include a bearing base positioned between the base and the bearing. The platform may rotate on the bearing relative to the base and the bearing base. The one or more weight sensors may be positioned between the base and the bearing base. One or more clamps may attach to the base and the bearing base may include one or more tabs extending therefrom configured to be respectively received within clamp slots of the one or more clamps to substantially limit rotation of the bearing base relative to the base. The one or more tabs may contact an upper wall of the one or more clamp slots when a load is not positioned on the platform.

In any of the above or another example, the one or more clamp slots may taper upwardly to prevent sidewalls of the respective clamp slots from inhibiting limited downward movement of the one or more tabs within the clamp slots when a load is positioned on the platform. The one or more clamp slots may include slots sleeves comprising a compressible elastomeric material configured to engage the one or more tabs received within respective clamp slots when a load is not positioned on the platform.

In any of the above or another example, a post may extend downwardly from an upper wall of at least one of the one or more clamp slot and a slot defined in at least one of the one or more tabs configured to receive the post when the tab is received with the clamp slot. The post may be dimensioned to move within the slot when a load is placed onto or removed from the platform.

In any of the above or another example, the one or more weight sensors comprise one or more load cells. The one or more load cells include contact surfaces for engaging contact surfaces of the bearing base. In one configuration, the one or more load cells include contact surfaces for engaging contact surfaces of the one or more load cells.

In any of the above or another example, the infant sleep device includes a drive system including a motor operable to rotate the platform above the base.

In another aspect, an infant sleep device includes a platform, a base, one or more weight sensors, and a controller. The base may be configured to support the platform, and the platform may be configured to support an infant. The one or more weight sensors may be positioned to measure weight of an infant positioned on the platform. The controller may be configured to receive weight data from the one or more weight sensors and include an analysis module for analyzing the weight data.

In one example, the analysis module is configured to determine a feeding state of the infant, track weight of the infant over time, generate a weight profile, identify rapid weight gain or weight loss, identify abnormal weight change patterns, or combination thereof.

In still another aspect, a method includes measuring weight of an infant positioned on a platform of a sleep device with one or more weight sensors positioned to measure loads placed on the platform; transmitting the measured weight data to an analysis module; analyzing the measured weight data with the analysis module, wherein analyzing comprises comparing the measured weight data to previously measured weight data and determining a feeding state of the infant; and outputting an indication of the feeding state to a user interface.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

The present application discloses systems and methods for measuring infant weight. In some embodiments, infant weight is measured within a sleep device wherein the measuring system is incorporated with the sleep device. The present application also discloses systems and methods of analyzing collected infant weight and/or movements alone or together with additional infant data, which may be measured by one or more additional sensors or otherwise input into the system.

Infants spend most of their day asleep and lack the ability to clearly communicate information regarding their health and satiation state while awake. One of, if not the primary, method of communication that infants use to provide information about themselves is crying. However, crying and general fussiness are generic to many conditions the infant may experience, such as unsatisfaction, pain, fatigue, frustration, boredom, sickness, and hunger. In this regard, infant weight or weight patterns may be an important indicator of the health of an infant. Weight may also provide information that may be analyzed to determine feeding patterns and current satiation or feeding state. While the subject from which weight is to be measured is referred to herein as an infant, it is to be appreciated that infant may include a baby or child. Movement(s) may also provide information that may be analyzed to determine restlessness, or lack thereof, and specific movement patterns that may be indicators of medical conditions. Furthermore, various teachings herein may similarly find application to measuring and monitoring weight of adults.

Figure 1:
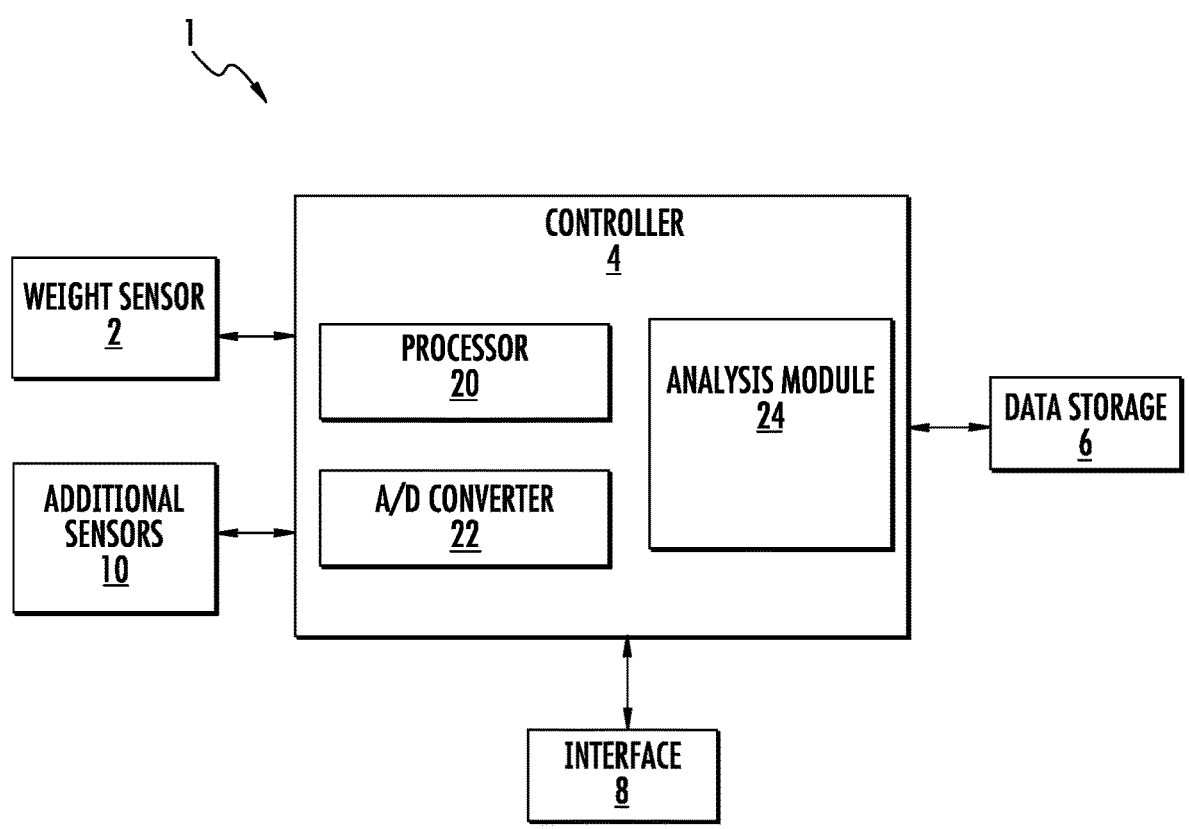
FIG. 1 schematically illustrates a weight detection system according to various embodiments described herein.

FIG. 1 schematically illustrates an embodiment of a weight detection system 1. The weight detection system 1 may include or operatively associate with a weight sensor. For example, the weight detection system 1 may receive and/or analyze weight data measured by one or more weight sensors 2. Weight sensors 2 may include load cells, strain gauges, compression sensors, or other weight sensor configurations.

In various embodiments, the weight detection system 1 is associated with a sleep device (not shown). For example, the weight sensor 2 may be configured to measure weight of a baby positioned on a sleep platform of the sleep device. It will be appreciated that while the weight detection system 1 is generally described herein with respect to measuring weight of an infant in a sleep device, in various embodiments, one, more, or all the operations and functionalities described herein with respect to the weight detection system 1 may be independent of a sleep device.

The weight sensor 2 may operatively communicate directly or indirectly with a controller 4 including one or more processors 20 via wired and/or wireless communication protocols. The processor 20 may be local or remote and configured to execute instructions to perform the operations and functionalities described herein with respect to the controller 4. In one example, the weight sensor 2 includes a communication port comprising a wireless transmitter or transceiver that transmits detected weight data directly or indirectly to a communication port of the controller 4, which may comprise a wireless receiver or transceiver. In another or further example, the weight sensor 2 and controller 4 directly or indirectly transmit data therebetween via wired communication ports.

As introduced above, the controller 4 may include various communication ports for receiving and/or transmitting data, processing modules for processing data, signal converters and/or filters, and/or data generators configured to perform the operations of the controller 4. For example, one or more weight sensors 2 or additional sensors 10 may transmit detected data to the controller 4 for collection, processing, analysis, and/or further transmission. The controller 4 includes a processor 20, which may include a remote processor, configured to execute instructions to perform the operations and functionalities described herein with respect to the controller 4. In the illustrated example, the controller 4 is configured to receive analog data and convert all or a portion of the analog data to digital format. For example, detected data may comprise analog data and the controller 4 may include an analog-to-digital (A/D) converter 22 configured to convert the analog data to digital format. The controller 4 may include an analysis module 24 configured to analyze the collected data, such as weight data detected by one or more weight sensors 2.

The controller 4 may be local or remote with respect to the weight sensor 2 and/or a sleep device. For example, the controller 4 may be attached to or located on or proximate the weight sensor 2 and/or sleep device in which the weight sensor 2 measures weight. In another example, the controller 4 is remote with respect to the weight sensor 2 and/or sleep device. In such configurations, the weight sensor 2 may communicate with the controller 4 directly or indirectly, e.g., one or more intermediate communication devices such as RF, near field, cellular, Wi-Fi, and/or Bluetooth receivers, transmitters, or transceivers; smart home hubs; modems, Wi-Fi enabled devices; or wired networks and/or wireless networks. In some embodiments, the controller 4 may transmit collected data, e.g., weight data, detected data, and/or user input data, to a data storage medium 6. In one embodiment, all or a portion of the controller 4 and/or data storage medium 6 may comprise one or more servers or cloud networks configured to archive and/or analyze the collected data.

In various embodiments, the analysis module 24 may analyze weight data together with other collected data such as user input data and/or data collected from one or more additional sensors 10 positioned to collect data associated with an infant and/or surrounding environment. In some embodiments, the analysis module 24 may receive data other than detected data collected from sensors 2, 10 and/or data input by a user. For example, the controller may receive new or updated data models, data analysis from remote resources, and/or analysis tools/protocols. In these or other embodiments, the analysis module 24 includes a modeling engine configured to apply machine learning and/or AI processing to the data to generate outputs described herein. In one embodiment, the modeling engine includes or integrates data input and/or collected data from other controllers or sources. For example, multiple controllers 4 associated with multiple weight detection systems 1 and/or sleep devices may provide data to the controller 4 and/or a central resource for analysis by the analysis module 24 or modeling engine thereof.

In one embodiment, the controller 4 is distributed such that one or more processing and/or analysis functions are executed locally and one or more processing and/or analysis functions are executed remotely. For example, the controller 4 may receive and analyze weight data and/or other collected data locally and/or transmit all or a portion of the collected data and/or analyzed data to a remote processor or central or back-end resource for archiving, further analysis, use in data modeling relating to the infant or population trends and/or comparative analyses relating to a plurality of infants, or in other operations. In one embodiment, collected data can be transmitted to a back-end system for further analysis and historical storage. In such analysis, population trends and individual historical trends can be performed. In a further or another example, analyses may include comparative analysis of individuals versus population. In some embodiments, the controller 4 transmits inputted, raw, and/or analyzed data to a central resource, which may comprise a back-end system, for input or analysis together with inputted, raw, and/or analyzed data obtained by other weight detection systems. In one example, the central resource and the collective weight detection systems comprise a network wherein all or a portion of the data collected and/or analyzed may be shared. The data collected from the collective of weight detection systems may be used to generate new data models or update current data models, which may be subsequently utilized to improve analysis operations of the analysis module 4. It is to be understood that weight sensor 2 may be configured to directly and/or indirectly transmit weight data to a central or remote resource instead of or in addition to transmitting the weight data to controller 4.

Weight sensor 2 may be configured to collect weight data continuously, periodically, at predetermined intervals, upon receiving an instruction to collect weight data, and/or upon the occurrence of an event, such as when an infant is placed on the platform, e.g., after predetermined period after additional weight is detected on the platform. A user may initiate an initial weight measurement by communicating with a user interface 8 to indicate that the infant is positioned on the platform and a measurement is to be taken. In one embodiment, a user may define or schedule when weight measurements are to be taken or input an instruction via a user interface to collect weight data. In one embodiment, the weight sensor 2 and/or controller 4 may calibrate the weight sensor 2, e.g., upon startup to zero out the weight of the platform and any added materials, such as mattress, bedding, etc. As such materials altering weight measured by sensor may vary during use, the weight sensor 2 and/or controller 4 may be configured to re-calibrate at regular intervals. Alternatively or additionally, in some configurations, the weight sensor 2 and/or controller 4 may initiate a re-calibration automatically if the processor 20 determines that the weight of the system has changed when the infant is not present.

Controller 4 may transmit, directly or indirectly, collected data and/or generated outputs of the analysis module 24 and/or modeling engine, to a user interface 8. The user interface 8 may be local or remote with respect to the weight sensor 2, sleep device, or controller 4. The user interface 8 may comprise a display, buttons, switches, knobs, data ports, etc. for interfacing with the system 1, e.g., inputting information, providing instructions, personalizing, adjusting controller settings such as weight collection scheduling, and/or reviewing output analysis data. In some embodiments, the user interface is locally mounted to or positioned on the sleep device. In this or another embodiment, the user interface 8 may include a user device, such as a computer, tablet, smartphone, or dedicated device. The user interface 8 may be implemented utilizing an application executed by the user device or a device in communication with the user device.

The interface 8 may allow a user to input data such as date of birth of an infant, gestation age at birth, medical conditions, due date of an infant, name or an identifier for the infant, sex, weight of the infant, and the like. Initial weight data of the infant may be input manually or automatically. In some embodiments, the inputs may be used to select or identify a suitable infant weight profile or initial weight profile from which an individualized weight profile is built by the system 1. Additional inputs may include information inputs. Information inputs may include infant weights, lengths, circumferences, travel, immunizations, illness, heart rate, respiratory rate, blood oxygenation, and the like. Infant weights may include weight at birth, weights taken at different weighings, weights taken over time, weights taken at predetermined times and/or intervals, and the like. Lengths may include baby length at birth, length at different times, length or change in length over time, length measurements taken at predetermined times and/or intervals, and the like. Circumferences may include circumference of the head at birth, circumference at different measurements, circumference change over time, circumference measurements taken at predetermined times or intervals, and the like. Such length and circumferences may also be calculated automatically using sensors such as a pressure mat that detects pressure distribution and/or dimensions of applied pressure. Such other sensors may comprise additional sensors 10 incorporated with the weight detection system 1 or may be add-on or peripheral devices. For example, utilizing pressure mat data, the controller 4 may also calculate length or circumference. A pressure mat may be integrated with a mattress, positioned one a mattress, or positioned between the platform and a mattress. The user interface 8 may be an integral part of the sleep device, and/or a separate piece, such as on a mobile peripheral device, which may be connected by a wired connection, a wireless connection, and the like to the sleep device. Wireless connection may be a Wi-Fi connection, Bluetooth connection, and the like. The user interface 8 may have controls, set-up information input, and other input data that can be sent to the control system 1 of the device. Controls may include an on/off control, sound control, motion control, light control, and the like. Controls may be enabled or disabled.

In some embodiments, a user interface may include a mobile application executed on a computer, tablet, dedicated device, or smartphone. The mobile application may provide data to the user. Data may include monitoring data, feedback data, control data, reporting data, analytics data, statistics, and the like. The mobile application may be installed on a mobile device. The device may be a smartphone, tablet computer, and the like. The mobile device may have an operating system that may be iOS, Android, and the like. The mobile application may enable interactions with the controller 4. Interactions may be enabled through a communication interface. The communication interface may be a universal serial bus (USB) interface, Wi-Fi interface, Bluetooth interface, and the like. Interactions may be control interactions. Control interactions may be similar to the interactions that may be enabled directly from the sleep device, only available on the mobile application, and the like.

Other mobile device interactions may include reports and statistics, sharing and group interactions, benchmarking and comparison interactions, graphic interactions, data upload to a third party interactions, feedback from a subject matter expert interactions, warning alert interactions, journal sharing/printout interactions, weight interactions, breastfeeding interactions, camera interactions, and the like. Other input interactions may include photo input interactions, video input interactions, audio input interactions, and the like. Weight detection system outputs, which may include notifications, from the controller 4 or application in communication with the controller 4 or data collected thereby may be directed to interface 8, which may be mounted on the sleep device or may be or include a separate device, such as a smartphone, tablet, or other communication device as introduced above. The weight detection system 4 may be configured to communicate via a Wi-Fi connection, cellular, land line communication, or other communication connection route for transmitting data and/or message communications, e.g., calls, emails, alerts, text messages, posts, etc. For example, the controller 4 may be configured to transmit signals and/or data communications according to a compatible communication protocol for routing the message.

In some embodiments, the analysis module 24 is configured to track infant presence on the platform. Presence tracking may utilize one or more weight sensors, such as one or more of a load cell, gyro, strain gauge, piezo sensor, resistive potentiometer, or accelerometer. Weight sensors may also be utilized for motion tracking. For example, the analysis module 24 may track positioning of an infant on the platform by analyzing weight data for changes in weight applied to the platform.

Messaging may be applied to presence tracking. For example, a notification may be transmitted to a user interface 8, which may include a computer or smartphone app, when a large increase or decrease in weight is detected. Messages may be transmitted to provide notification of presence or absence/removal of an infant from the platform.

Analysis of weight increases or decreases may be set to identify one or more of a momentary weight increase or decrease or fluctuations, a weight increase or decrease over one or more time periods, sustained weight increases or decreases, and/or rapid increases, decrease, or fluctuations. An instantaneous sustained increase in weight, for example, from a steady state weight corresponding to weight of an infant may indicate presence of an infant on the platform. An instantaneous sustained decrease in weight from a steady state, which may include a steady state during which infant presence was determined, may indicate that the infant has been removed or displaced from the platform. A sustained increase in weight following detection of presence of an infant may indicate that something has been positioned on or fallen onto the platform, which may pose a danger to the infant.

Additionally or alternatively, the analysis module 24 may utilize weight data for movement tracking. For example, rapid, slow, brief, extended, methodical, repetitive, or haphazard weight fluctuations above and below a baseline weight may indicate movement of the infant. Such movement may be related to kicking, rolling, writhing, wiggling, coughing, and/or arm or head movement. Movement(s) may also provide information that may be analyzed to determine restlessness, or lack thereof, and specific movement patterns that may be indicators of medical conditions. Detection of such movements may trigger transmission of messages to a user interface 8 or initiation of an alarm. In some embodiments, the analysis module 24 may be configured to analyze weight data associated with movement to identify restlessness and/or physical distress and provide a notification or alarm of the same. Physical distress, for example, may be a pre-cursor to SIDS, choke hazards, or dangerous positioning of an infant. The analysis module 24 may utilize predefined patterns and/or thresholds of weight fluctuations indicative of physical distress to identify physical distress instances.

In some implementations the analysis module 24 analyzes motion and/or weight fluctuation data together with data collected by additional sensors 10. Utilization of additional sensors 10 may enhance accuracy of determination of events or conditions or may provide deeper analysis to determine other events or conditions. For example, audio data collected by sound sensors (e.g., one or more microphones) may be used to detect physical distress. In a further example, the analysis module 24 analyzes motion data and audio data to detect if an infant is choking by pairing or correlating motion and sound consistent with choking. In yet another example, the analysis module 24 analyzes motion and breathing or respiration data to detect if an infant is choking by pairing or correlating motion with lack of breathing or respiration consistent with choking.

In various embodiments, users may define sensitivity of presence and/or movement tracking features to track large and/or small weight changes or momentary fluctuations. In an example, using a user interface 8, a user may define one or more lengths of time over which weight changes or fluctuations are to be measured for tracking purposes. For example, an average, range, or sum weight change or fluctuation over a specified or predetermined period of time may be used by the analysis module 24 as part of a messaging scheme wherein a threshold amount, range, average, and/or sum of weight change or fluctuation over one or more time periods may trigger a message notification. In some configurations, thresholds may be static, preset, or a user may select among two or more sensitivity settings that define threshold weight changes and/or fluctuations of one or more predetermined periods of time.

Other types of presence and/or motion tracking may be used instead or supplemental to presence and/or motion tracking utilizing weight sensors. For example, optical sensors, e.g., infrared, video, motion, or light sensors, may track motion and/or presence or absence of an infant and/or provide data for analysis together with weight data.

In various embodiments, messages related to weight data or analysis thereof may be routed to one or more of an alert system, caregiver, user communication device, emergency services, hospital, or third party resource. Messages may be transmitted, for example, as text messages, SMS, push notification, voice messaging, etc. As introduced above, messages may relate to presence detection or removal of the infant from platform of a sleep device. For example, a message notification may be transmitted to a user device or interface 8 such as a computer or smartphone when the presence of the infant is detected or when the controller 4 determines the infant has been removed. In another or further example, the system 1 may provide users with preference settings that allow a user to set preferences with respect to how, when, and to what device such notifications are to be transmitted. The settings may be set and accessed via a user device or interface 8, such as with a smartphone application. The controller 4 may also be configured to initiate an alarm sound when removal of an infant is detected. Such a notification system may also be set to inform the caregiver if the infant has lost or gained more weight than a preset limit (taking events such as feeding and bowl movements into account). In one embodiment, the system 1 may integrate with and/or communicate with health care/hospital monitoring systems. For example, the system 1 may provide raw or processed data, notifications, and/or alerts to third party systems. The system 1 may also integrate with third party systems.

In various embodiments, raw or analyzed data may be provided to a user, e.g., parent or caregiver via the user interface 8. The data may be used to or reflect tracking of weight changes over time or provide presence information, such as notifications and duration spent in the device. In this or another example, weight changes and/or patterns identified in the data by the analysis module 24 may be used to better understand feeding patterns, weight patterns, and/or build a weight profile with respect to the infant. For instance, an infant will typically spend a majority of its day sleeping or otherwise in the sleep device. The analysis may analyze weight data to determine a feeding state. For example, weight data may be compared to previously collected weight data to determine if the infant is underfed, overfed, or properly fed and/or satiated. In some embodiments, the analysis module 24 may be configured to predict if the infant had a diaper change, was fed or not in the sleep device for other reasons. For example, such data may be provided to a caregiver for tracking purposes, which may be helpful in identification of behavioral patterns or underlying medical conditions. As part of an above or another analysis, the analysis module 24 may incorporate predictive analyses to improve data interpretation capabilities. For example, when a measured weight is identified to have dropped between proximate or sequential measurements, the analysis module 24 may be configured to consider whether the difference in measured weight may be related to a diaper change between measurements. Proximate measurements may be within a predetermined number of measurements such as two or three. The analysis module 24 may utilize previous proximate or sequential weight measurement drops or programed ranges to identify such potential events and may monitor proximate or subsequent measurements for confirmation. In a similar manner, the analysis module 24 may be configured to account for items positioned on the weight sensor 2 while the infant is positioned on the sensor. For example, the analysis module 24 may track deviations in weight during time periods the infant is on the platform. Thus, if the infant is given a bottle while positioned on the weight sensor, the concomitant weight change may be tracked and compared to weight before, during, and after. Any of the above analyses may also consider other data collected such as sleep duration, sleep quality, or behavior state associated with previous weight measurements or may compare the weight data to a weight pattern, general or personalized weight profile, or threshold values.

Determination of behavior state may utilize weight data collected from weight sensors 2 such as momentary weight fluctuations between proximate or sequential measurements indicative of movement. For example, high frequency or larger frequent changes in detected weight may indicate an infant is in an agitated or upset state, while low frequency or smaller fluctuations may indicate a more relaxed or soothed state, and minimal weight sensor changes may indicate a sleep state. In some embodiments, determination of behavior state uses other collected data in addition to or instead of analysis of momentary weight fluctuations. For example, the controller 4 may include one or more additional sensors 10 to provide data to the analysis module 24 for use in determining a behavior state such as motion sensors (e.g., optical, accelerometers, video), sound sensors (e.g., microphone), biological sensors such as breath sensors to detect heart ration and/or breathing rate or depth, and/or other sensors for detection of other biological parameters (e.g., blood pressure). Analysis indicating an agitated or upset state may include detection of loud and/or high pitched sounds or crying, rapid movement, increased blood pressure and/or breathing indicative of an agitated or upset state while decreased sound, motion, blood pressure, and/or breathing may indicate a relaxed or soothed state or sleep state. Such analyses may be temporally overlaid with collected weight data to improve accuracy of a behavior state determination and/or correlation of weight patterns with behavior state, sleep duration, or sleep quality. In further or other embodiments, the collected data includes length and/or circumference data with respect to the infant. Length and/or circumference data may be input by a user, e.g., at a user interface, and/or collected by additional sensors 10.

The analysis module 24 may correlate weight data and, optionally, input data and/or data collected from other sensors 10 or other infants, with sleep patterns to help advise the user of feeding frequencies and amounts. For example, while infants may typically be soothed when upset by combinations of movements, swaddling, comforting, or audio or visual stimuli, it has been found that a hungry infant may be somewhat immune to such attempts to soothe. By tracking weight and/or weight patterns of an infant overtime, it is possible to inform a user that an infant may be hungry or underfed and, thus, feeding the infant should be considered as a manner of soothing the infant. The data collected may also be analyzed to determine the restlessness of the infant. Restlessness may be determined from rapid variations in weight as measured by the weight sensor that are indicative of movement. For example, frequency and amplitude or degree of weight variations or patterns measured thereof may be used to characterize movements. In one embodiment, weight data may be analyzed to determine if the infant is in distress. For example, the controller 4 may analyze weight data to identify movements indicating the infant is in distress, a condition that could be an indicator of SIDS/SUID, choking, seizure or other concerns. The response to a determination that the infant is in distress, the controller 4 may initiate a notification to a caregiver or emergency service as described above. Alternately or additionally, the controller 4 may initiate an audible alarm to alert a caregiver. Alternatively or in addition to one or more of the above, the controller 4 may output signals to the motor operable to move the platform. The signals may cause the motor to move the platform in a jolting motion pattern.

Further to the above, collected weight data and, optionally, input data and/or data collected from other sensors 10 or other infants may be used as a health indicator. For example, rapid weight gain may be associated with overeating, medical conditions such as hormonal conditions, impending illness or medication. The collected weight data may be tracked over time for analysis by the analysis module 24. In one example, the weight data, which may include a weight profile generated therefrom, is compared to standardized growth tables or charts to determine if a significant deviation in growth rate is present.

In various embodiments, the analysis module 24 may be configured to identify abnormal infant weight or growth rates and/or respond to abnormal infant weight or growth rates. Abnormal infant weight may be identified as an instance wherein a weight of an infant deviates from an expected or desired weight changes. Expected or desired weight may be that of the weight of the infant if fed or optimally fed for sleep or satiation. In one example, identification of abnormal infant growth rate may include detecting with one or more sensors infant data such as infant weight. Identification of abnormal infant growth rate may also consider input data such as age of the infant, sex, medical conditions, amount fed over time, food type, or other infant data that may be input into the system 1. The infant data may be collected and analyzed by the analysis module 24 to identify a weight, growth rate, or a deviation from an expected weight or growth rate pattern. Weight or growth rate patterns may be compared to general or individualized weight or growth rate profiles to identify abnormal deviations. In some embodiments, profiles may be individualized to a particular infant, generic, or may be selected based on characteristics of an infant, which may be input by a user or detected and/or measured by the weight detection system 1. In one example, the controller 4 includes or may access multiple profiles that may be selected for use by the analysis module 24 based on medical history; an input age, which may include whether and/or to what extent the infant was born premature or late; weight, e.g., birth weight and/or current weight; sex; whether the infant is breast fed, formula fed, or combination or ratio thereof; existence of known medical conditions; medications; whether the mother smokes; and/or other data associated with the infant.

In an embodiment, the controller 4 may individualize a weight or growth rate profile from a generic or selected profile during an infant's use of the weight detection system 1. For example, the system 1 may measure and analyze weight, which may include weight patterns at certain times, such as throughout a day and/or over periods of time such as hours, days, weeks, or months, and update a profile to individualize an initial profile. Upon determination that abnormal weight or growth rate is present, the weight detection system 1 may be configured to generate a notification signal. The signal may comprise a sound emitted from a speaker or visual indication such as a light or display on one or more user interfaces 8. Sound notifications may include recorded or generated messages providing information regarding the notification and/or data prompting the notification signal. Visual notifications may include text displays, text displays in an associated application or on another user interface, email messages, or text messages, for example. The sound, light, or display may be provided on the sleep device on which the weight sensor 2 measures infant weight or may be provided by another device, e.g., a user device, such as a computer, tablet, smartphone, dedicated remote device, or smart home device. In various embodiments, the weight detection system 1 and/or controller 4 includes or interfaces with, e.g., operatively communicates with, such user devices directly or indirectly via wireless communication protocols, which may include Bluetooth, Wi-Fi, or cellular, for example. In one example, the controller 4 is configured to transmit raw or analyzed weight data and, optionally, other collected data to a data storage 6 medium and/or central resource, as introduced above, configured to analyze the data.

As introduced above, in some embodiments, determining a weight profile includes identifying one or more weight patterns associated with the infant. For example, weight patterns may be analyzed with respect to events such as instances or patterns of sleep, breathing, heart rate, ambient temperature, body temperature, fussy or upset state, and/or combinations thereof. Temporal deviations in weight prior to, during, and/or after events may be used to identify optimal weights for promoting or avoiding such events. That is, infant weight may be related to feeding patterns, which may include time of day of feeding, amount fed, time since last feeding, time since last bowel movement, Analysis of weight and associated feeding patterns may be used to identify optimal feeding times and/or amounts to promote sleep, sleep duration, or sleep pattern characteristics. For example, if a user would like an infant to sleep a particular duration, the system 1 or an application executed with respect to a user device or interface 8 may suggest feeding the infant at one or more particular times and/or amounts of food to be fed prior to sleep. The user may also be alerted if collected data does not indicate that the infant has been sufficiently fed for facilitating sleep. In some embodiments, the analysis module 24 may analyze collected data such as type of food fed to the infant, which may be input into the system 1 by a user via the user interface 8. The analysis module 24 may correlate type of food consumed with past sleep instances to determine if particular foods facilitate sleep or satiation or are associated with poor sleep or fussy, irritable, or sick behaviors. In one such example, the analysis module 24 or application may output a suggestion with respect to feeding the infant a particular type of food or combination of foods. In some configurations, optimal amounts fed and/or feeding times may be suggested to be modified or increased to account for growth and development of the infant. In one application, the analysis module 4 may utilize weight data to determine if the infant is dehydrated. In some instances, the analysis module 4 may identify certain foods that trigger behaviors or collected data that are consistent with an allergic reaction. In some embodiments, the analysis module 4 may utilize machine learning or AI techniques the above or any other analyses.

In some embodiments, the system 1 may determine if the infant is fussy or upset by measuring sounds, heart rate, blood pressure, galvanic skin response, body temperature, and/or infant movement using microphones, accelerometers, optical sensors, infrared sensors, pressure gages, piezo electric sensors, electrodermal activity sensors. In some embodiments, the weight sensor 2 may be used to detect movements of the infant. For example, the weight sensor 2 may include multiple weight sensors 2 distributed at different locations along a sleep platform wherein changes in weight distribution among the weight sensors 2 may be used to detect movement. Detection of motion, such as a wiggling of infant, through signal processing and using other ancillary information can be used to determine if the infant is in distress. This can be critical information to have to determine SIDS. Movement detection may also be used to help determine restless sleeping patterns and be used as an indicator for other conditions. In some embodiments, the analysis module 24 may utilize detected data including weight data and one or more of sound data, motion data, sleep quality and/or duration, and temperature data along with input data with respect to food type to identify potential allergies that the infant may have.

In various embodiments, respiration sensors may include breath detection sensors, such as those described in U.S. patent application Ser. No. 16/905,424, filed Jun. 18, 2020, the contents of which are hereby incorporated by reference herein. Detection of breathing and breathing characteristics such as breathing rate, depth, intervals, and/or patterns thereof may be collected and analyzed together or separate from weight data.

As introduced above, the controller 4 may communicate with an application executable either directly or indirectly on a user device such as a computer, tablet, smart device, smartphone, or dedicated device. In some examples, the user device comprises all or a portion of the user interface 8. The application may interface with the controller 4 and/or analysis module 24 to track weight and/or other collected and/or analyzed data. In some embodiments, the analysis module 24 or application may be configured to generate a graph of weight changes over time or may provide feeding advice to the user based on analysis of the collected data. In one example, the analysis module 24 or application may generate or provide suggested feeding schedules and/or feeding amounts. For example, a feeding schedule may be output based on desired sleep time identified by a user or an optimal sleep time (time of day), duration, or quality. The feeding schedule may identify a time range and amount of food the infant is to be fed prior to one or more of the desired sleep events. In some embodiments, the amount of food recommended may be provide based on duration of the feeding, volume or weight of food, or weight increase of the infant. In one example, the controller 4 may be configured to notify the user, e.g., via the user interface 8, if the infant has been sufficiently fed according to the feeding schedule when the infant is positioned on the platform and weight of the infant is measured. The suggestions may be related to discrete feedings or multiple feedings. The suggestions may be related to modification or maintenance of growth and/or improving satiation. In one example, the analysis module 24 or application may be configured to identify potential medical conditions or deficiencies, which may be presented to a pediatrician for further consideration or clarification.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example network or system is applicable to software, firmware, and hardware implementations.

In accordance with various embodiments of the present disclosure, the processes described herein may be intended for operation as software programs running on a computer processor. Furthermore, software implementations can include, but are not limited to, distributed processing or component/object distributed processing, parallel processing, cloud processing, or virtual machine processing that may be constructed to implement the methods described herein. In one example, collected infant data, which may include input data, is transmitted directly to a weight detection module comprising a remote data processing resource or may be transmitted to a connection module for transmission to a data processing resource. The data processing resource may comprise a remote processor, which may be distributed, cloud-based, virtual, and/or comprise a remote application or program executable on a server, for example. The infant data may comprise raw infant data or raw motion data. In one example, the collected infant data transmitted may be preprocessed or partially preprocessed. For example, the collected infant data may be filtered locally at the sensor or a local processing unit and comprise filtered motion data, sound data, pressure/weight data, or combination thereof. A cloud-based service may comprise a public, private, or hybrid cloud processing resource. In an embodiment, the infant data signal processing may be performed on the backend of such a system. For example, all or a portion of the weight detection logic may be in the cloud rather than local, e.g., associated with a bassinet or other device in proximity to the infant being monitored. The backend may similarly be configured to generate and/or initiate alerts based on the data processing, e.g., comparison of current breathing to a general or customized weight profile.

In one embodiment, a weight detection system, or controller thereof, includes a remote resource such as a processor, application, program, or the like configured to receive collected infant data. The service may process and analyze the infant data as described herein, e.g., filter data, generate weight profiles, modify or update weight profiles, compare weight or weight patterns to general or customized weight profiles, determine if current weight or growth is abnormal, communicate and/or integrate with hospital monitoring systems or other third party systems, and/or generate or initiate alerts, e.g., phone call, email, light, sounds, motions, text messages, SMS, or push notifications. As noted above, the remote resource may comprise a cloud-based service.

The present disclosure describes various modules, which may also be referred to as sub-modules, systems, subsystems, components, units, and the like. Such modules may include functionally related hardware, instructions, firmware, or software. Modules may include physical or logical grouping of functionally related applications, services, resources, assets, systems, programs, databases, or the like. Modules or hardware storing instructions or configured to execute functionalities of the modules may be physically located in one or more physical locations. For example, modules may be distributed across one or more networks, systems, devices, or combination thereof. It will be appreciated that the various functionalities of these features may be modular, distributed, and/or integrated over one or more physical devices. It will be appreciated that such logical partitions may not correspond to physical partitions of the data. For example, all or portions of various modules may reside or be distributed among one or more hardware locations.

Various embodiments described herein may include a machine-readable medium containing instructions such that a device connected to the communications network, another network, or a combination thereof, can send or receive voice, video or data, and communicate over the communications network, another network, or a combination thereof, using the instructions. The instructions may further be transmitted or received over the communications network, another network, or a combination thereof, via the network interface device. The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure. The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The weight system described with respect to FIG. 1 may be utilized in a variety of sleep devices and hardware configurations configured to measure weight of an infant in the sleep device. For example, FIGS. 2-9, 11, and FIGS. 16-19 depict various embodiments of sleep devices including weight systems 1 and components thereof. The features described with respect to the various embodiments are not limited to such embodiments and those having skill in the art will appreciate that the various features may be used with each other in multiple combinations of such embodiments. It will also be appreciated that other configurations may be utilized to perform the functions of the weight detection system and the present application is not limited to utilization as configured in the exemplary embodiments.

Figure 2:
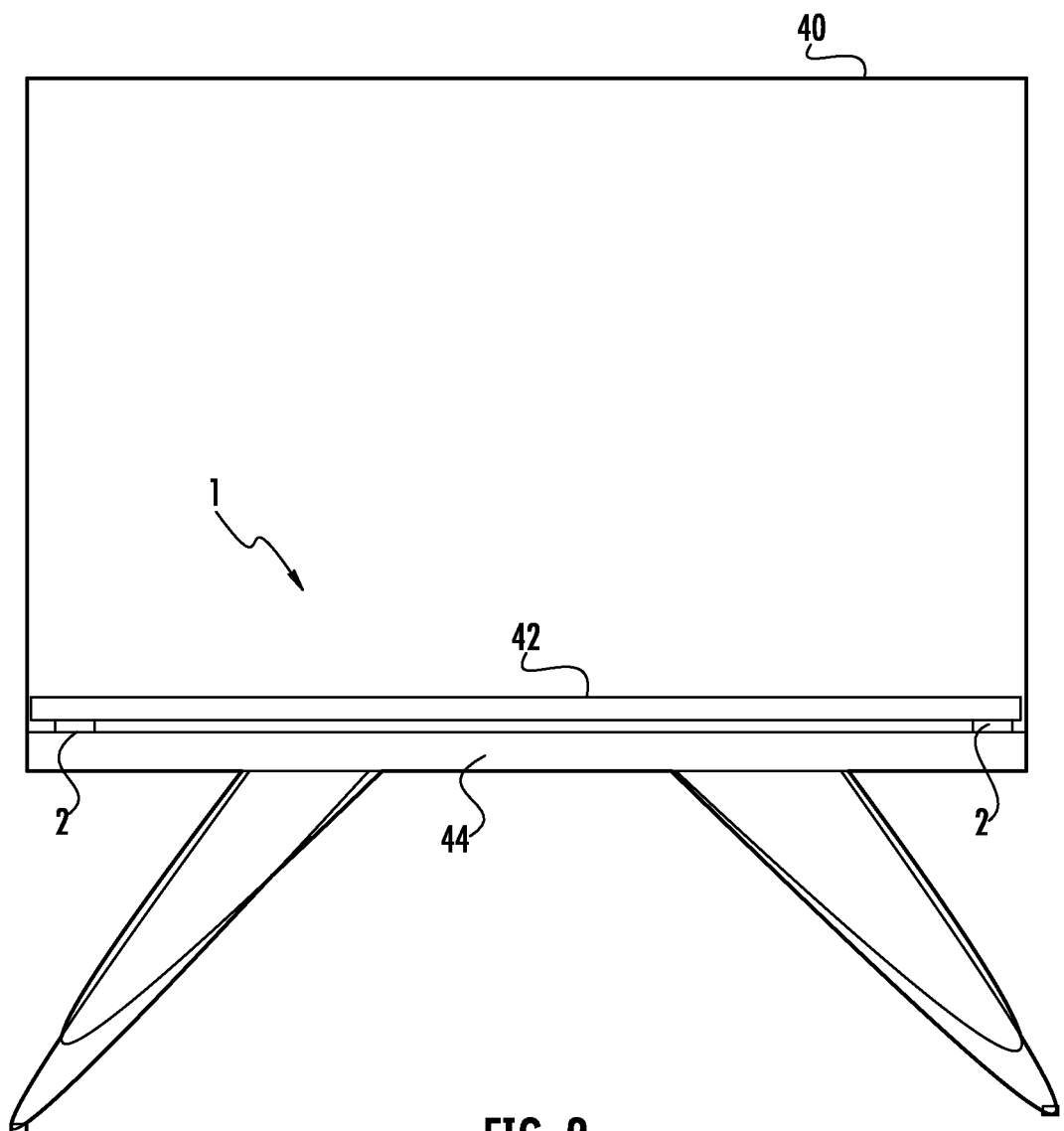
FIG. 2 illustrates a weight detection system or components thereof incorporated with a sleep device according to various embodiments described herein.

FIG. 2 illustrates an example configuration of a weight sensor 2 of the weight detection system 1 integrated with a sleep device 40 according to various embodiments. The sleep device 40 comprises a bassinet in this embodiment, but other sleep device 40 configurations may be used with respect to the illustrated embodiment as well as the other exemplary embodiments described herein. In the illustrated embodiment, two or more weight sensors 2 are positioned between a platform 42 configured to support an infant and a base 44 configured to support the platform 42. The weight sensors 2 are positioned around a perimeter of the platform 42. In some embodiments, additional weight sensors 2 may be used at other perimeter and/or more central locations of the platform 42. For example, weight sensors 2 may be positioned under the platform 42 at an upper right region, an upper left region, a lower right region, and a lower left region. In one embodiment, one or more weight sensors 2 may be positioned at one or more central locations of the platform 42 instead of or in addition to weight sensors 2 positioned along a perimeter of the platform 42. The weight sensors 2 may include load cells, strain gauges, compression sensors, or other weight sensor device configurations.

Figure 3:
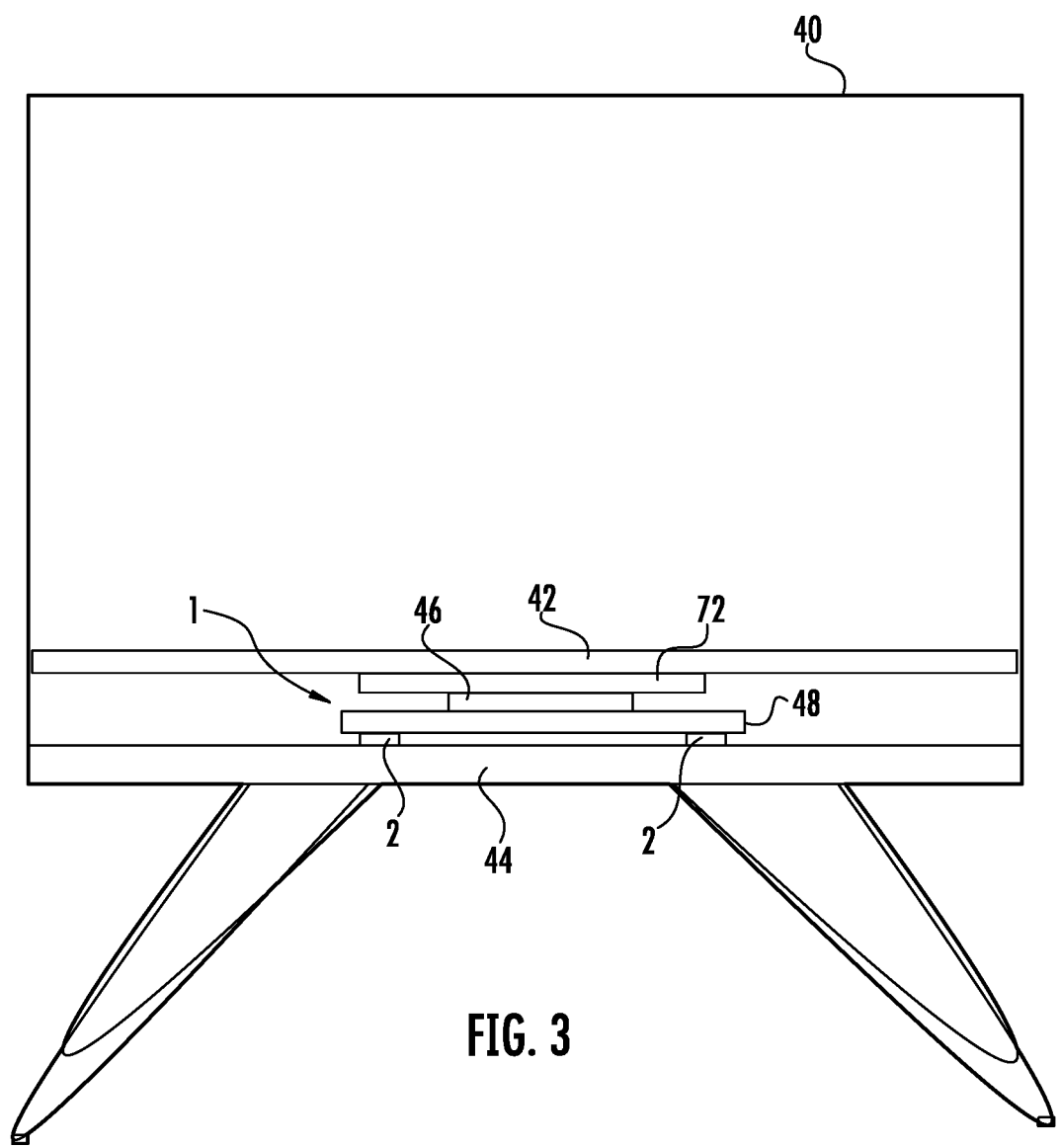
FIG. 3 illustrates a weight detection system or components thereof incorporated with a sleep device according to various embodiments described herein.

As introduced above, and with reference to FIG. 3, in some embodiments, the weight detection system 1 may be utilized with a sleep device 40 having a platform 42 configured to move relative to a base 44. In various embodiments, the sleep device 40 may be similar to that described in U.S. patent application Ser. No. 14/448,679, filed Apr. 31, 2014, or U.S. patent application Ser. No. 15/055,077, filed Feb. 26, 2016, both of which are incorporated herein. Thus, the weight may be configured to be accurately measured on a platform 42 configured to move relative to the base 44. In various embodiments, the platform 42 may be movably supported over the base 44 by a bearing or actuator, for example. In the illustrated embodiment, the platform 42 is rotationally supported over the base 44 by a bearing 46. A bearing base 48 may be positioned between the base 44 and the bearing 46. The bearing 46 may be structurally associated with the bearing base 48, platform 42 or attachment thereof, or may be a separate structure coupled between the platform 42 and the bearing base 48. The bearing base 48 may position over the one or more weight sensors 2. When an infant is positioned on the platform 42, the force may be transferred to the one or more weight sensors 2 configured to collect weight data. The weight data may be transmitted to the controller via wired or wireless communication protocols, as described in more detail above and elsewhere herein.

With continued reference to FIGS. 2 & 3, weight sensors 2 may collect weight data continuously, periodically, at predetermined intervals, upon receiving an instruction via a user interface to collect weight data, upon the occurrence of an event, such as when an infant is placed on the platform 42, prior to movement of the platform 42, when the platform 42 is moving, when movement of the infant is detected or has stopped for a predetermined period of time.

FIGS. 4-9 illustrates example components of a sleep device and weight detection system according FIG. 3.

Figure 4:
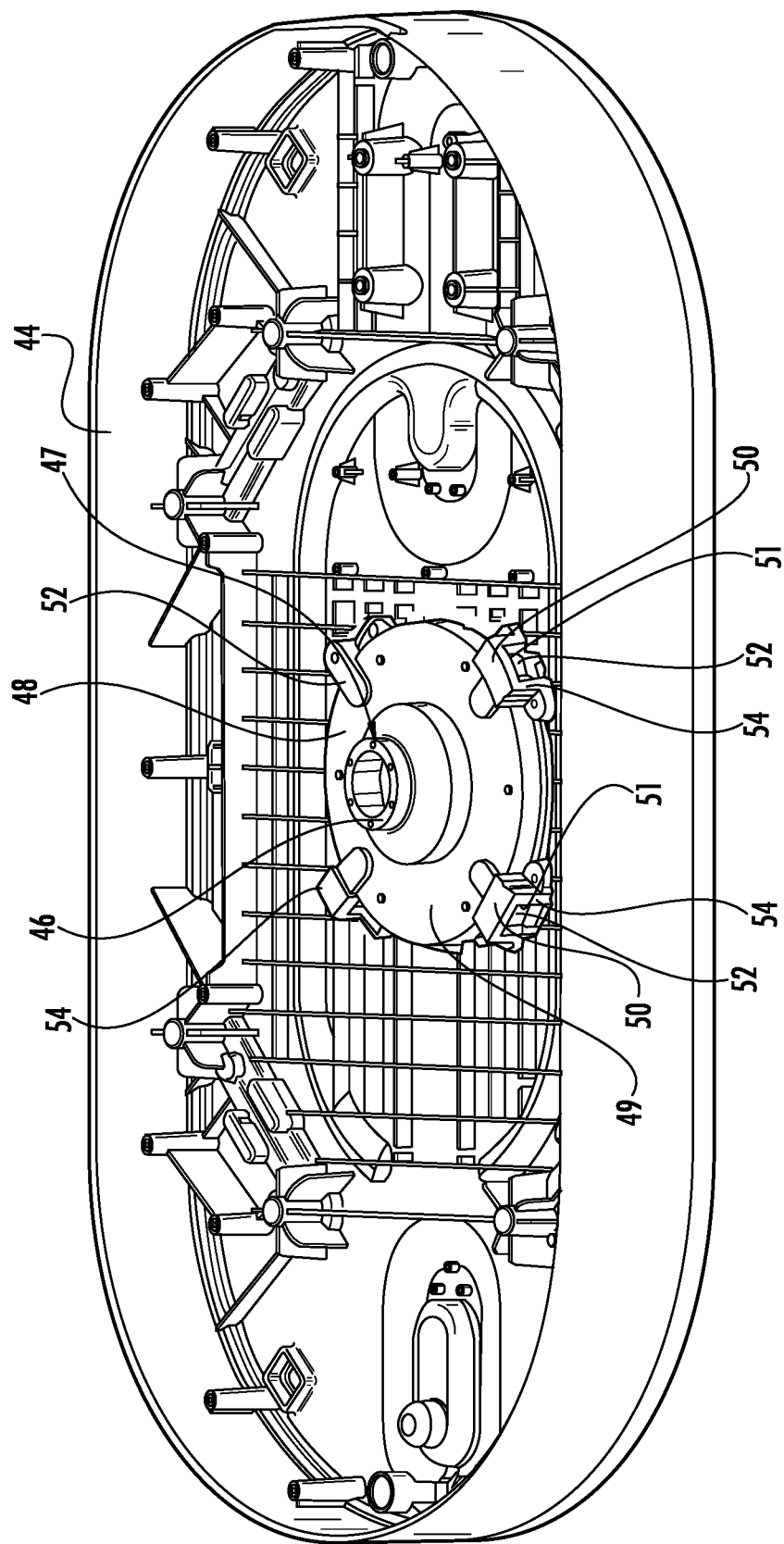
FIG. 4 is a perspective view of various components of a weight detection system positioned within a base portion of a sleep device including a bearing base and clamps for constraining movement of the bearing base according to various embodiments described herein.

FIG. 4 is a partial assembly including a bearing base 48 positioned over a base 44 of the bassinet with the platform removed. A bearing 46, not shown, is positioned on the bearing base 48 and is rotatable relative to the bearing base 48. The bearing 46 includes mounts 47 for rotatably mounting a platform, not shown, over the base 44. Any manner of translating force to rotate the platform may be used. In some embodiments, rotational force may be transmitted to the platform by a motor (not shown) or other force translator. In one example, a motor having a post that receives the motor output is located below the bearing base 48 and the post extends through the bearing 46 and connects to the platform to translate rotational motion output of the motor to the platform. In another example, the motor is located at another position within the base 44 and translates its output to the platform at a position offset from the center of the bearing 46. For example, the post may rotate along a track that extends along the platform to rotate the platform on the bearing 46, for example, in a manner similar to that described in U.S. patent application Ser. No. 15/055,077, filed Feb. 26, 2016. In another example, the motor is positioned on the platform and the post rotates along a track that extends along the base 44 to rotate the platform on the bearing 46. In another example, one or more belts or pulleys are used to translate rotational motor output to the platform. In another example, the motor outputs longitudinal force or the motor output is converted to longitudinal force that is transmitted to the platform to rotate the platform on the bearing 46.

Clamps 50 may be used to maintain positioning of the bearing base 48. In the illustrated embodiment, the bearing base 48 includes tabs 52 that extend outwardly to position within clamp slots 51. Clamp slots 51 are dimensioned to receive tabs 52 and prevent or limit lateral and longitudinal movement of the tabs 52 and hence the bearing base 48. FIG. 4 illustrates two clamps 50, each retaining a tab 52. The remaining tabs 52 are shown at various stages of assembly for clarity, however, when assembled for operation, each tab 52 will typically be received within a clamp slot 51. The upper right tab 52 is shown without a clamp 50 and the upper left tab 52 is shown received within a slot sleeve 54.

One or more slot sleeves 54 may be used to define the clamp slot 51. In various embodiments, slot sleeves 54 may be dimensioned to engage or closely approximate an adjacent profile of a tab 52 received within a clamp slot 51 to limit lateral and longitudinal movement. In one example, a slot sleeve 51 comprises an elastomeric compressible material or cushion to provide a soft interface between the clamp 50 and a tab 52 received within the clamp slot 51. It will be appreciated that in some embodiments the clamp 50 may not include a slot sleeve 54 and the clamp 50 may include one or more of the features of the slot sleeve 54 described herein. Additional or fewer tab 52 and clamp 50 combinations may be utilized.

Figure 5:
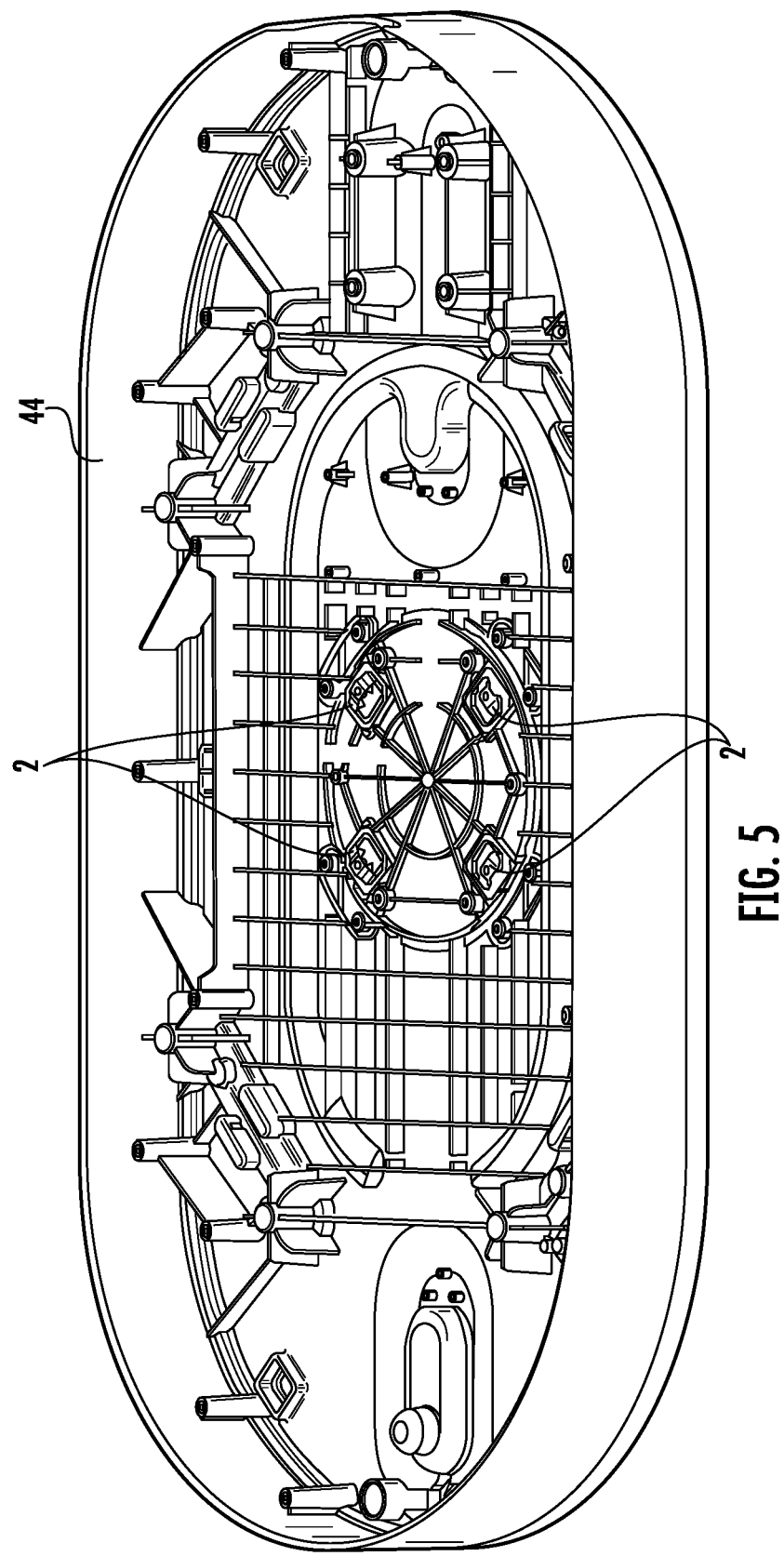
FIG. 5 is a perspective view of the components illustrated in FIG. 4 with the bearing base and clamps removed according to various embodiments described herein.

FIG. 5 illustrates the base 44 with the clamps 50 and bearing base 48 removed. The one or more weight sensors 2 are shown attached to the base 44 at locations below the bearing base 48 when installed. The illustrated weight sensors 2 comprise four load cells. The weight sensors 2 are preferably symmetrically distributed; however, in some embodiments non-symmetrical distribution of weight sensors 2 may be used.

Figure 6:
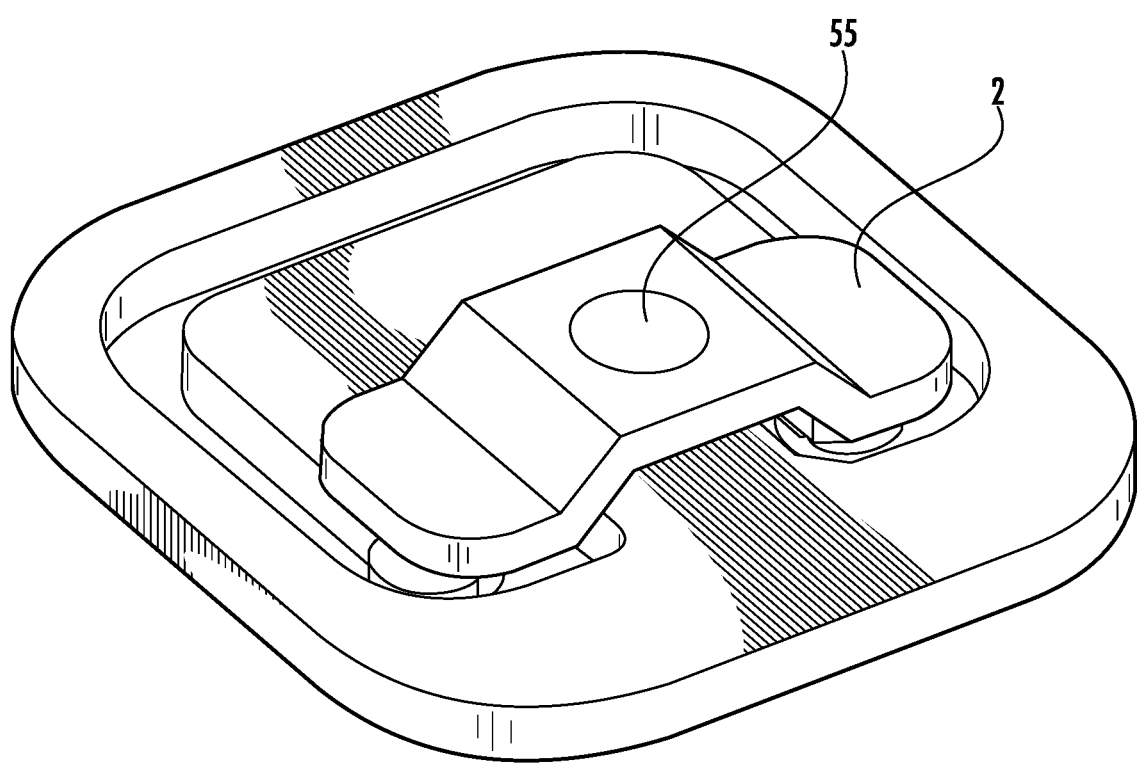
FIG. 6 is an isolated view of a weight sensor according to various embodiments described herein.

An isolated view of a weight sensor 2 is provided in FIG. 6. The sensor 2 comprises a load cell having a contact surface 55 for engaging a contact surface 56 (FIG. 7B) of the bearing base 48. The weight sensors 2 or controller, such as controller 4 described with respect to FIG. 1, may include an A/D converter. While other configurations may be used, load cells may be configured in a wheatstone bridge and be configured to feed resistance data to the A/D converter. In various embodiments, the weight sensor 2 and/or controller may be configured to calibrate at startup or prior to positioning of the infant on the platform in order to zero out the weight of the bed. The weight of the infant when positioned on the platform applies force to the load cells, causing the load cells to deform. This resulting change in resistance is read by the A/D converter and converted to a weight by the processor.

Figure 7A:
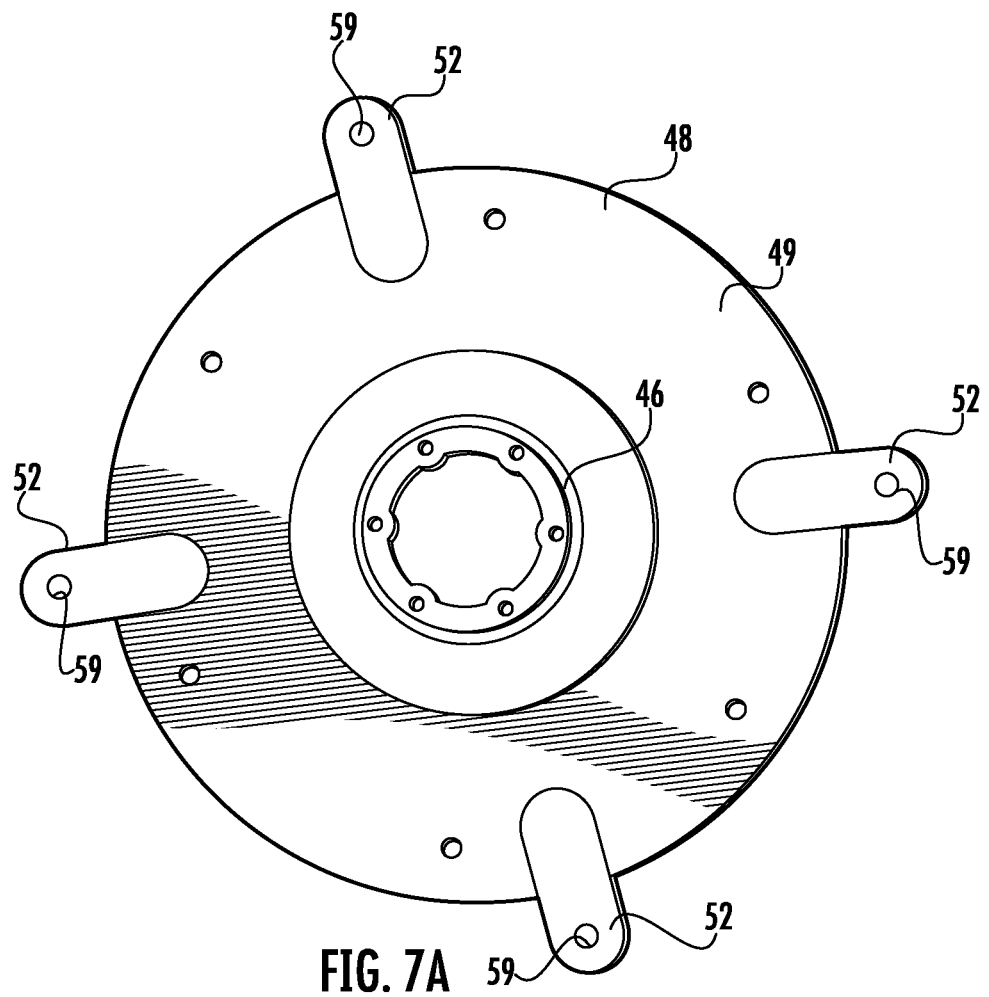
FIG. 7A is an isolated top view of a bearing base according to various embodiments described herein.
Figure 7B:
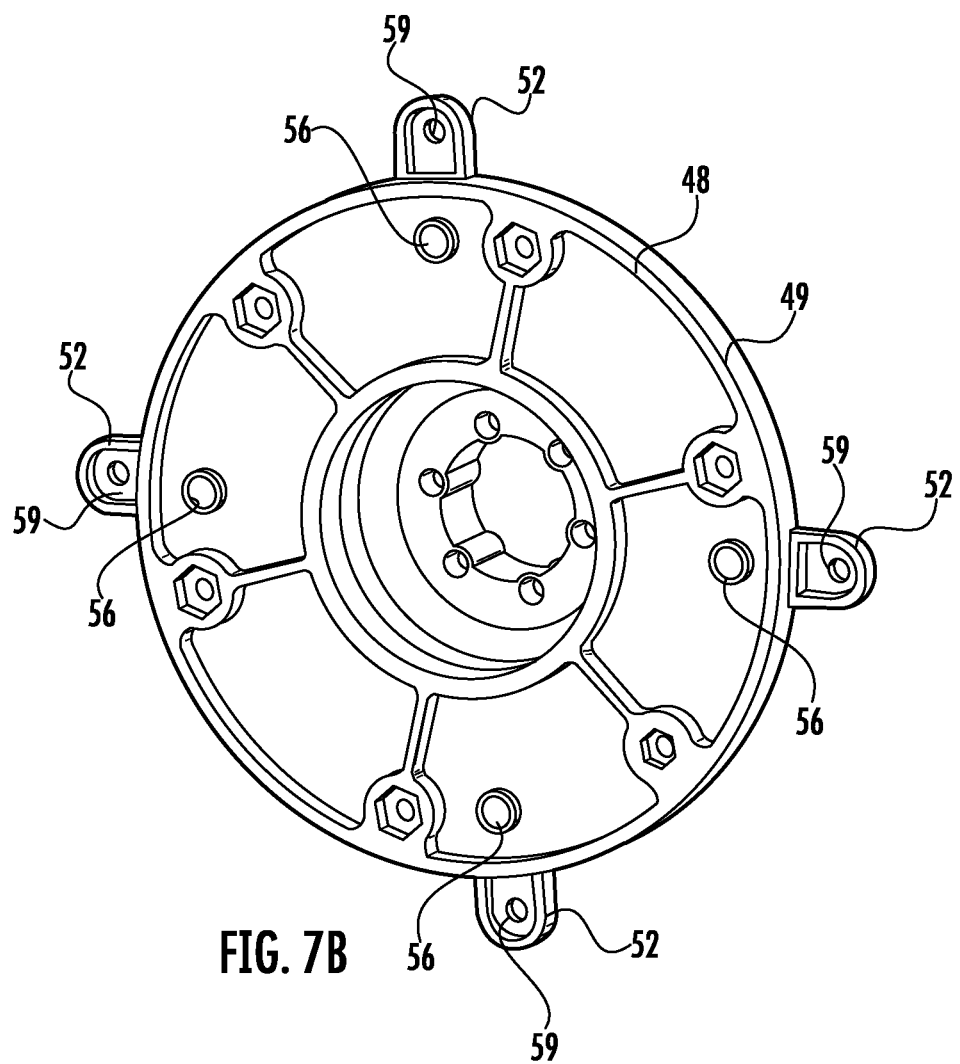
FIG. 7B is an isolated bottom view of a bearing base according to various embodiments described herein.

FIGS. 7A & 7B provide isolated upper and lower side views, respectively, of the bearing base 48. The bearing base 48 includes a body 49 and four tabs 52 that extend from the body 49. In other embodiments, fewer or additional tabs 52 may be used. The tabs 52 comprise oblong extensions but other profile shapes may be used. The body 49 includes contact surfaces 56 along an underside thereof for engaging weight sensor contact surfaces 55 (see, e.g., FIG. 6). The contact surfaces 55 for engaging the weight sensor contact surfaces 56 include sleeves 57 for receiving the raised surface along the contact surface 55 of the weight sensor 2 to provide consistent location of engagement. The surfaces that engage may include the raised surface along contact surface 55 or a perimeter thereof. Similarly, the surfaces that engage may include the sleeves 57 and/or surfaces within the sleeves 57. It is to be appreciated that other configurations may be used. For example, sleeves 57 may be excluded and/or other positioning structures may be used. Similarly, weight sensors need not include raised surfaces in some configurations and the bearing base 48 may contact weight sensors along flat or contoured surfaces, for example.

Figure 8:
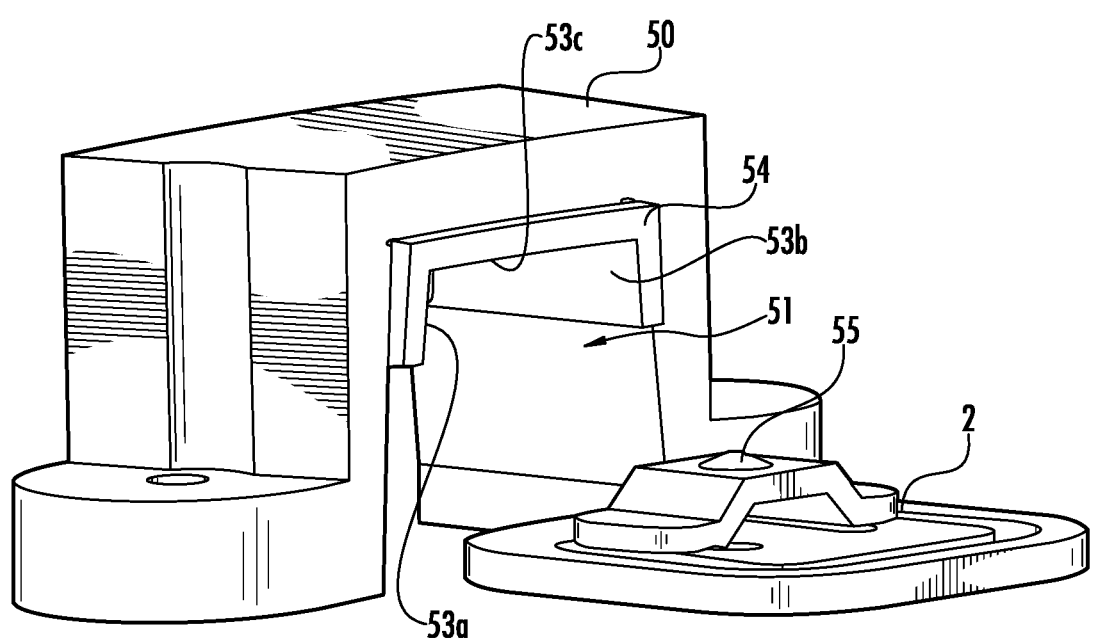
FIG. 8 is an isolated view of a clamp and weight sensor according to various embodiments described herein.

FIG. 8 is an isolated view of a clamp 50 positioned adjacent to a weight sensor 2. The slot sleeve 54 is positioned in clamp slot 51. When a tab 52 of the bearing base 48 is received within the clamp slot 51, the tab 52 is constrained from lateral and longitudinal movement by sidewalls 53a, 53b. Sidewalls of 53a, 53b of other clamp slots 51 may also cooperate to constrain lateral and longitudinal movement of the bearing base 48. For example, longitudinal movement may be constrained by clamp slots 51 having sidewalls 53a, 53b positioned laterally to the direction of force due to tabs 52 within such clamp slots 51 compressing against sidewalls 53a, 53b. Tabs 52 may also contact sidewalls 53a, 53b to prevent torque applied at the bearing 46 from rotating the bearing base 48. Depending on desired configuration and tolerances, lateral or longitudinal movement of the bearing base 48 may also be limited by positioning of clamps 50 relative to a perimeter of the bearing base 48. For example, a perimeter of the bearing base 44 may be positioned proximate to a clamp 52 such that the perimeter engages the clamp 50 when force is applied to the bearing base 48 in the direction of the clamp 50.

Figure 9:
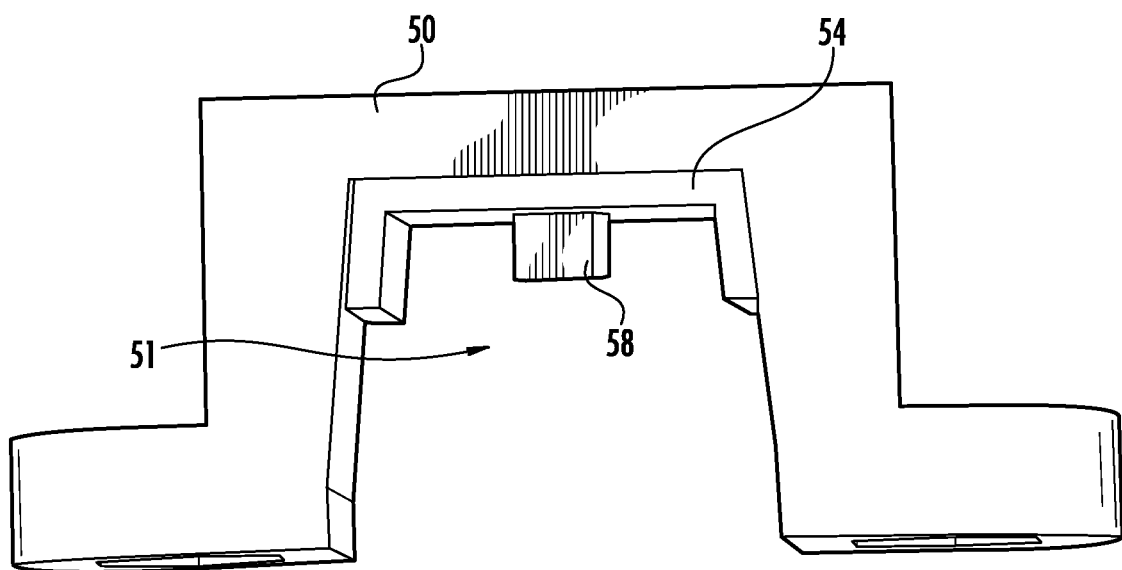
FIG. 9 is an isolated view of a clamp according to various embodiments described herein.

Tabs 52 may also be limited vertically, upward, by an upper wall 53c of the clamp slot 51. As best depicted in FIG. 9, the clamp slot 51 and/or slot sleeve 54 may include a taper toward upper wall 53c of the clamp slot 51. The taper may be dimensioned to manage tolerances and constrain max excursion of the tabs 52 and bearing base 48. In some embodiments, tabs 52 of the bearing base 48 may compress against one or more surfaces of the slot sleeve 54. For example, tabs 52 may compress against the upper wall 53c in the resting position, e.g., absent a load on the platform, to apply a slight load to one or more weight sensors 2 thereby maintaining a continuous load force on the one or more weight sensors 2 and position of the bearing base 48 over the one or more weight sensors 2. The taper may be configured to prevent sidewalls 53a, 53b from inhibiting downward vertical movement of tabs 52 while guiding the tabs 52 to a consistent maximum upper vertical position.

One or more rigid stabilizing structures may extend within or adjacent to clamp slots 51 to further stabilize the position of the bearing base 48 while also allowing an amount of vertical movement of the bearing base 48 relative to the base 44. The amount of vertical movement may be limited, e.g., to a few micrometers or a millimeter or less, to allow the bearing base 48 to apply a load force against one or more weight sensors 2. In one example, stabilizing structures include a rail and groove configuration wherein a tab 52 and clamp slot 51 include complementary rail and groove structures that guide the limited vertical translation of the tab 52 when received within the clamp slot 51. In the illustrated embodiment, a vertically extending stabilizing structure comprising a post 58 extends into the clamp slot 51. The post 58 is positioned to extend through a slot 60 (FIGS. 7A & 7B) defined through a tab 58. The post 58 is dimensioned to slide within the slot 60 with minimal resistance. The post 58 may provide a guide to vertical movement of the tab 52 within the clamp slot 51. Depending on desired configuration and tolerances of clamps 50 and the bearing base 48, posts 58 may also be used to constrain lateral and longitudinal movement of the bearing base 48.

In some embodiments, other stabilizing structures may be used to constrain lateral and/or longitudinal movement of the bearing base 48, which may be in addition or instead of the clamps 50 and/or tabs 52 described above with respect to FIGS. 4-9. For example, stops may extend from the base 44 and position around a perimeter of the bearing base 48 to constrain lateral and longitudinal movement. In one embodiment, the bearing base 48 may include one or more vertically extending slots for receiving a rigid structure that extends from the base 44. The rigid structure may allow some vertical movement while constraining lateral and longitudinal movement. In one example, the rigid structure comprises shoulder bolts, which may also be used to limit extent of upward vertical movement.

Figure 10:
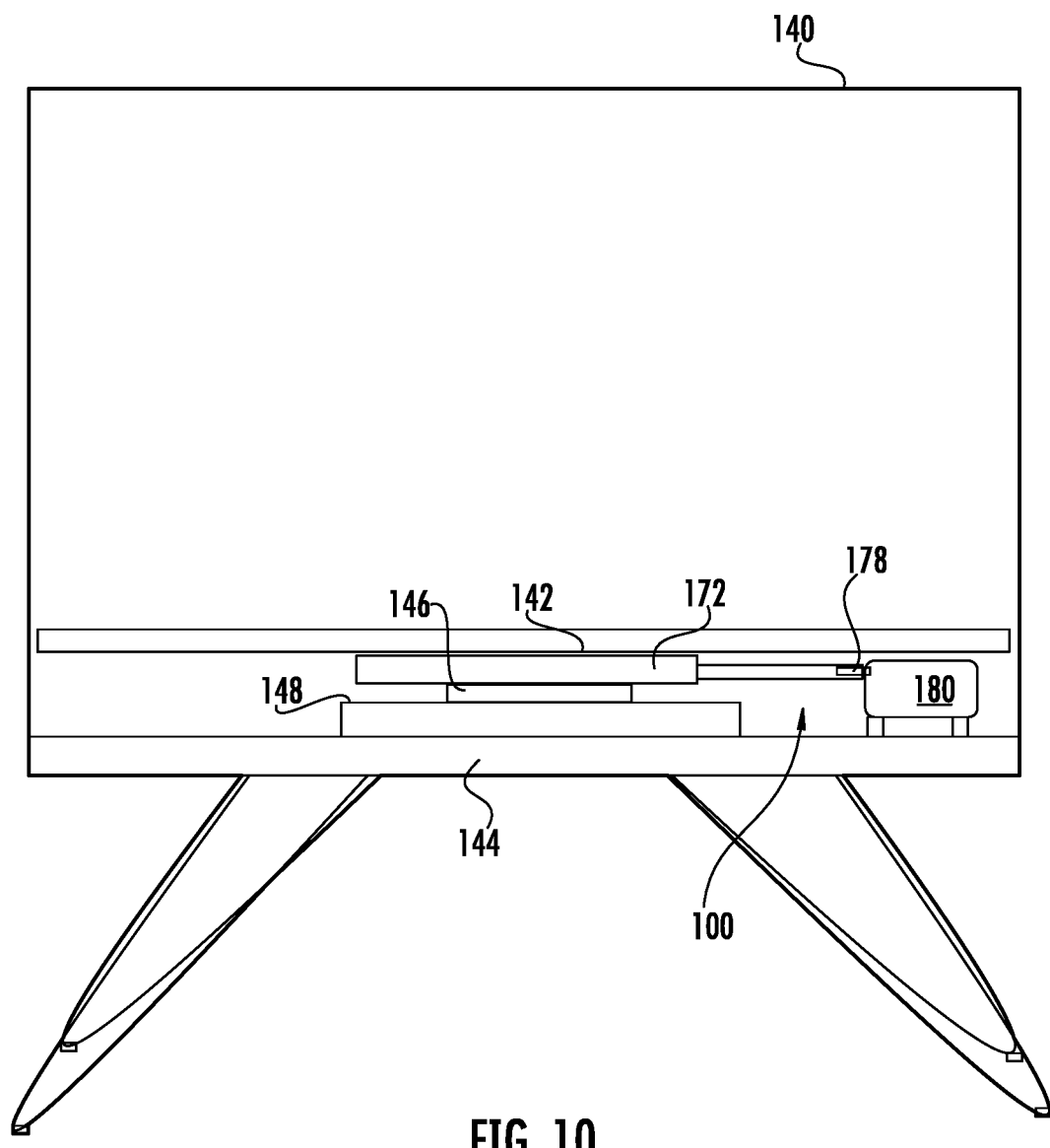
FIG. 10 illustrates a sleep device including a drive system according to various embodiments described herein.
Figure 11:
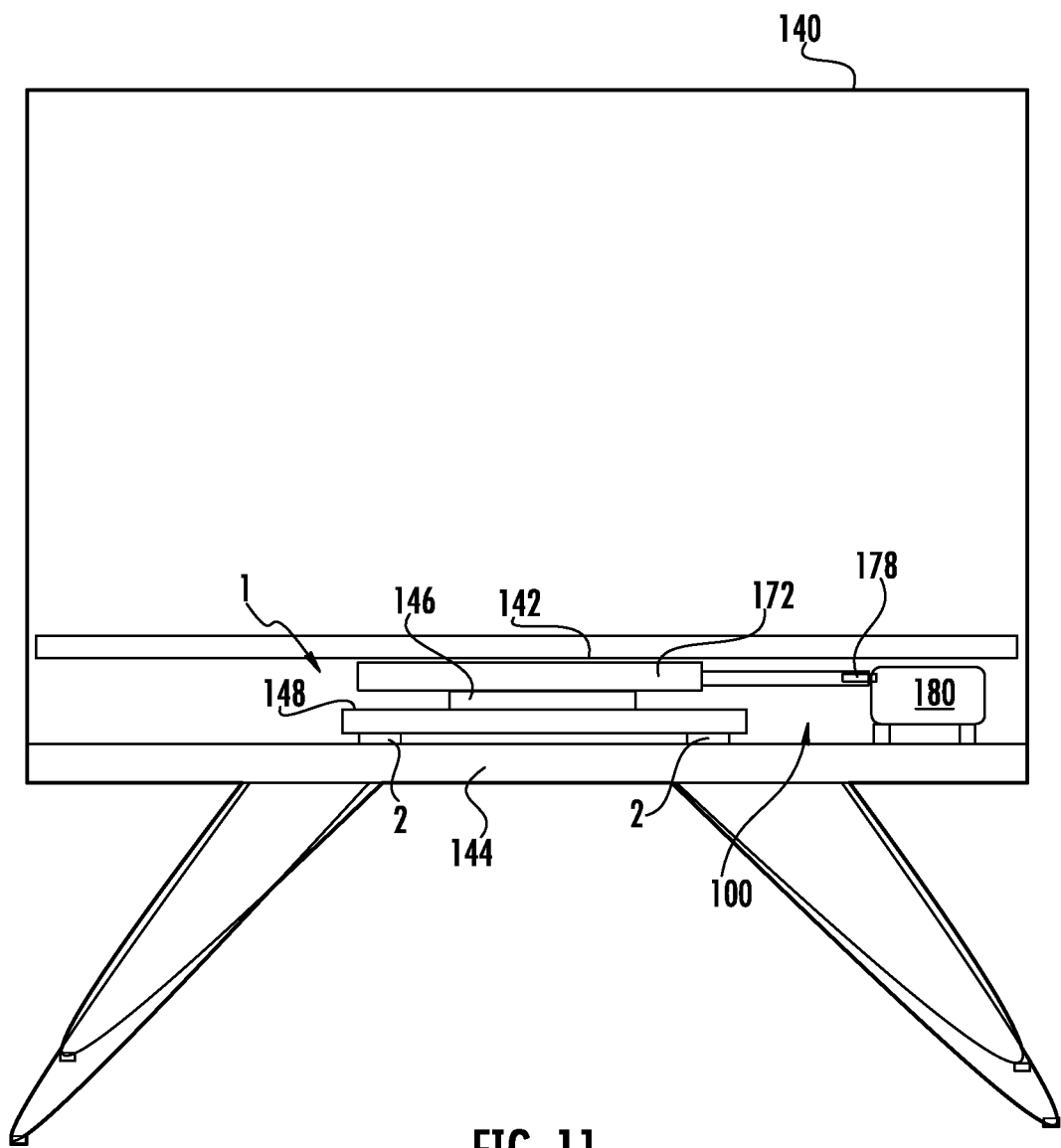
FIG. 11 illustrates a sleep device including a drive system including a weight detection system according to various embodiments described herein.
Figure 12:
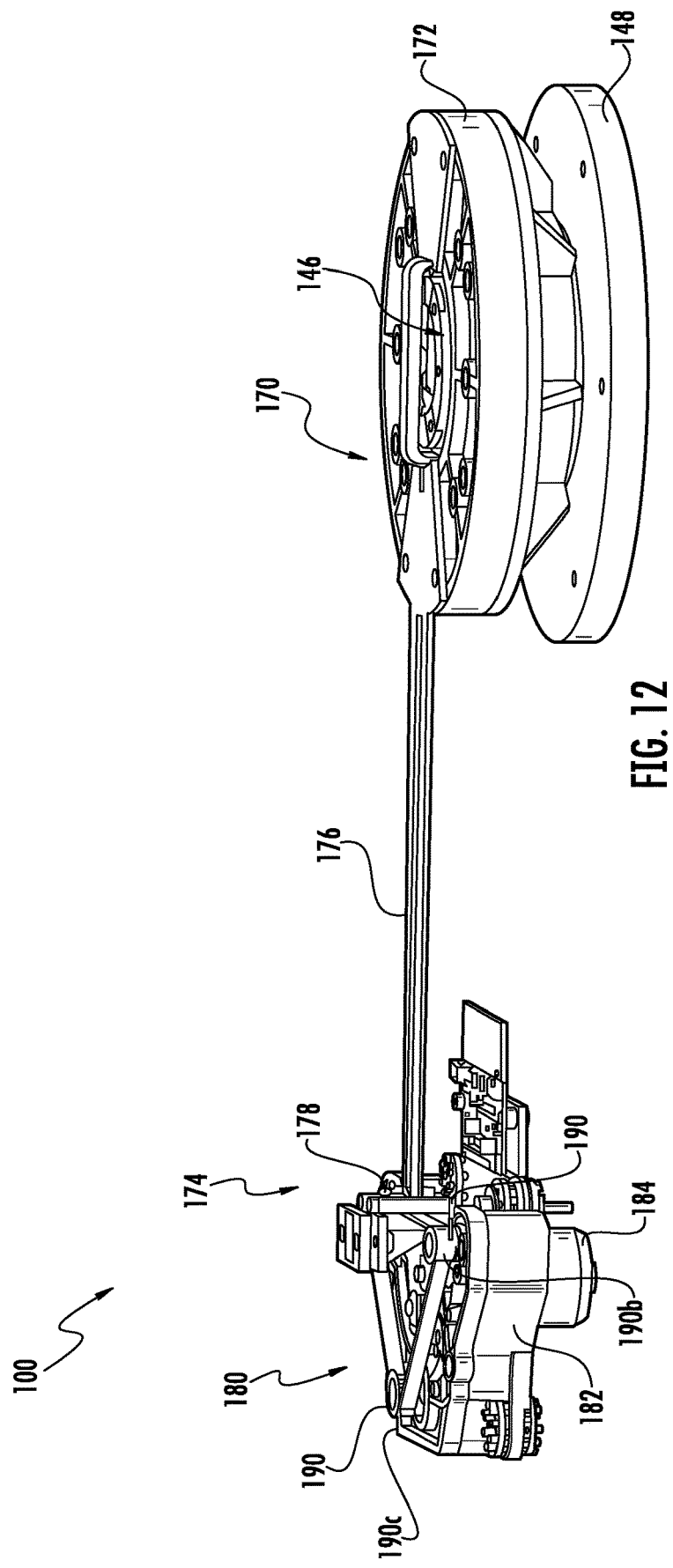
FIG. 12 illustrates a perspective view of a drive system according to various embodiments described herein.
Figure 13:
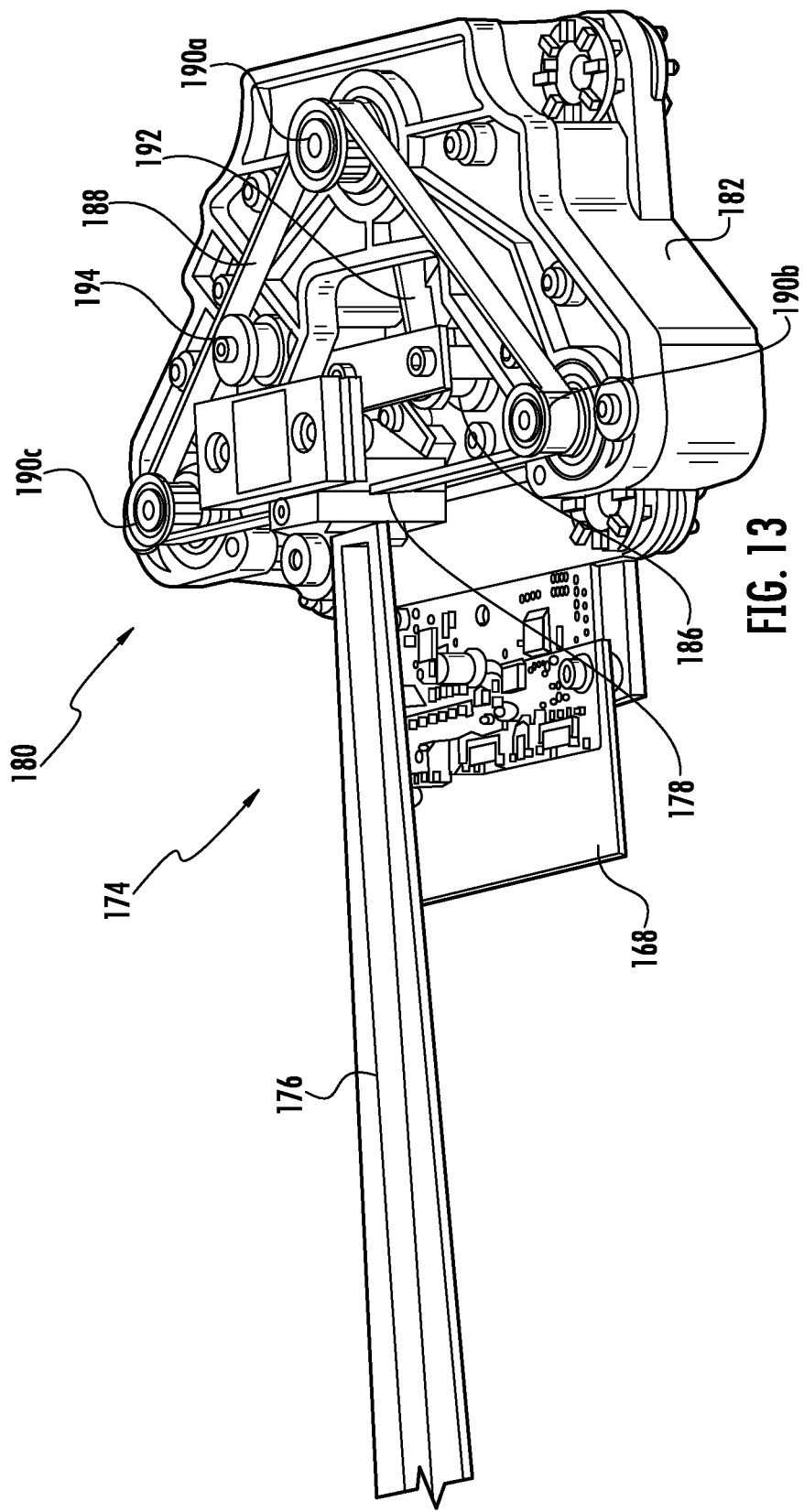
FIG. 13 illustrates an isolated view of the drive module and drive belt attachment assembly of a drive system according to various embodiments described herein.
Figure 14:
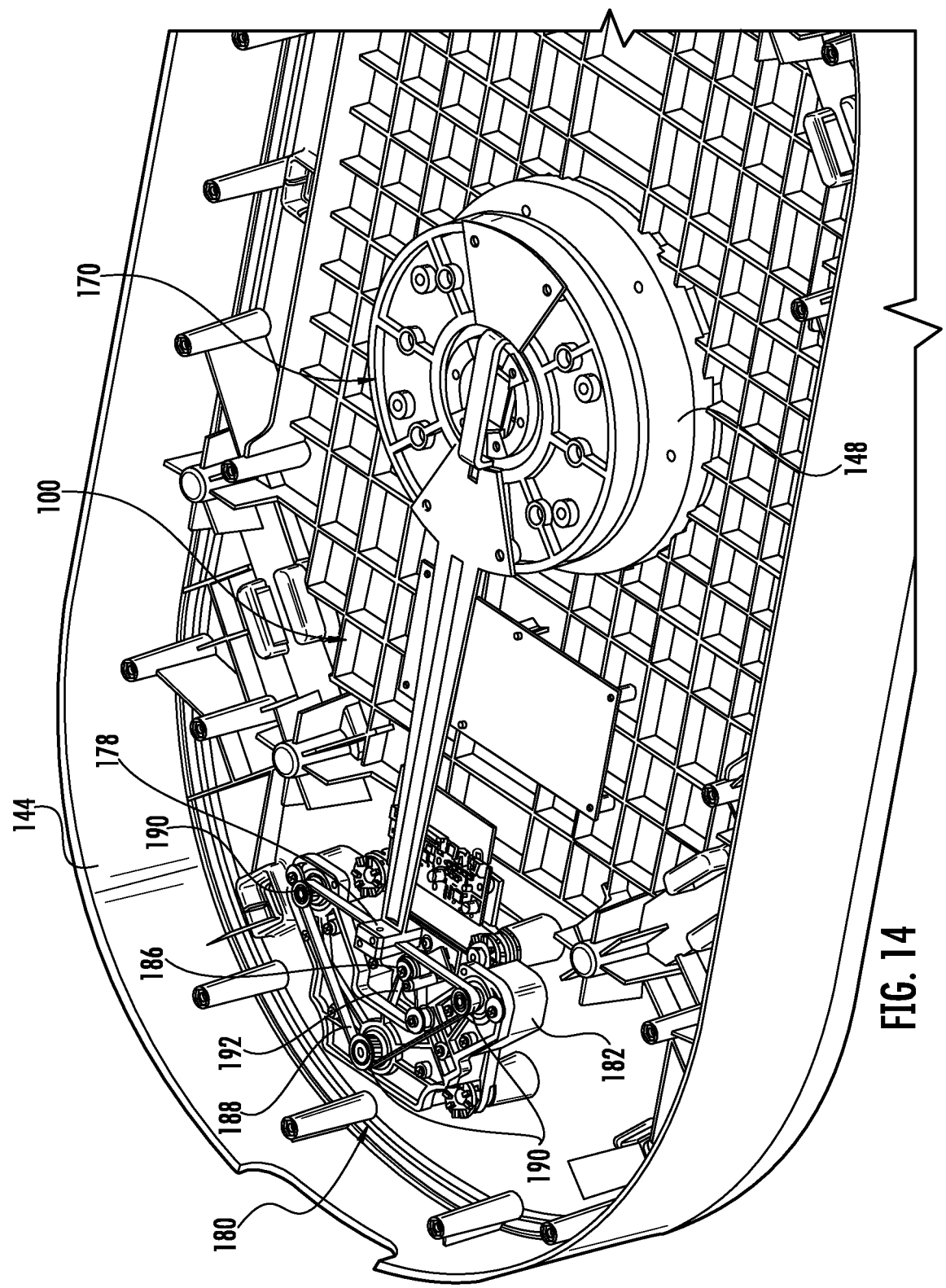
FIG. 14 illustrates a partial view of the drive system shown in FIG. 12 positioned within a base with certain components removed for clarity according to various embodiments described herein.
Figure 15:
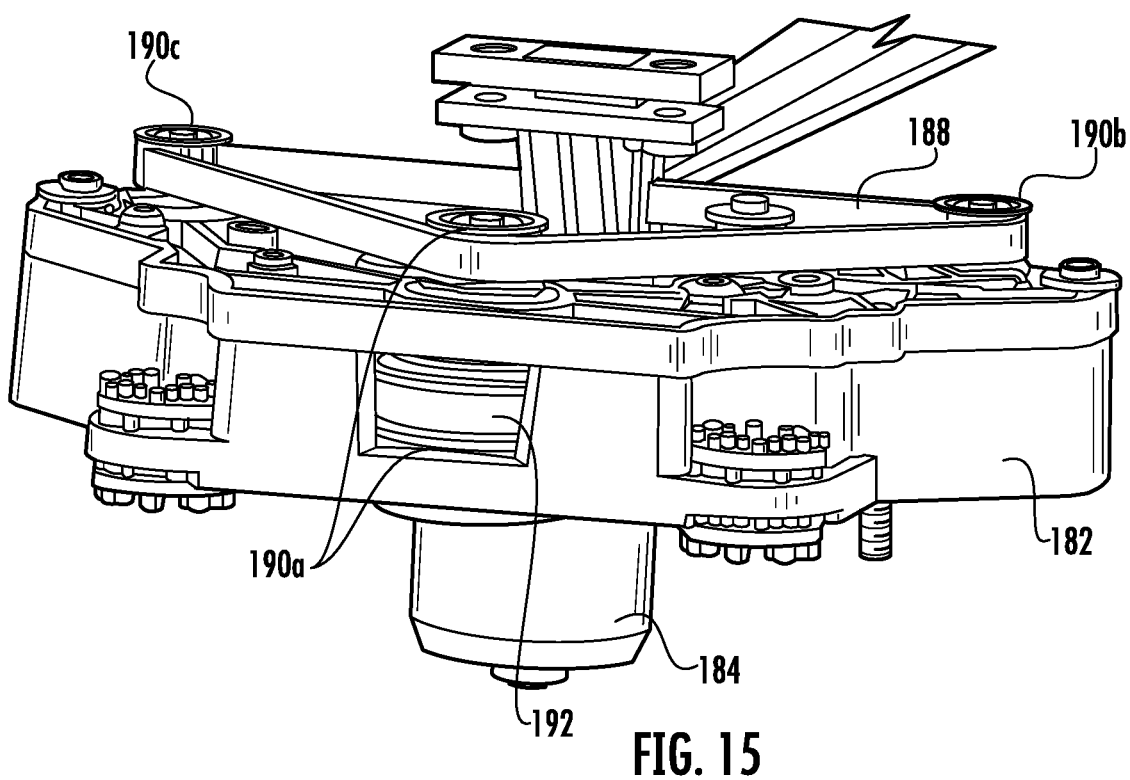
FIG. 15 illustrates another view of the drive module shown in FIG. 13 according to various embodiments described herein.

FIGS. 10-15 illustrate various embodiments and views of an example drive system 100 for a sleep device configured to rotate a platform 142. FIG. 10 illustrates the drive system 100 incorporated in a sleep device 140 including a weight detection system 1 as described herein with respect to FIGS. 2-9B. FIG. 11 illustrates the drive system 100 incorporated in a sleep device without a weight detection system. FIGS. 12-15 provide various views of the drive system 100.

The sleep device 140 may be similar to that shown in FIG. 3 and include a base 144. A bearing base 148 may be supported on the base 144 in a rotationally fixed position. For example, the bearing base 148 may be bolted to the base 144 or otherwise attached thereto. In some embodiments wherein the sleep device includes a weight detection system 1, the bearing base 148 may be supported on the base 144 via clamps (see, e.g., FIG. 4) that allow the bearing base 148 to apply downwardly directed force onto weight sensors 2 for detection of weight as described herein.

A bearing 146 couples between the bearing base 148 and the platform 142 (see, FIGS. 10 & 11) to allow rotational motion of the platform 142 relative to the bearing base 148. The bearing 146 may include a thrust bearing, a lazy Susan bearing, a slide bearing, plain or journal bearing, a low friction surface, a low friction Teflon surface, or a low friction silicon surface, for example. The platform 142 may be configured to rotate in a horizontal plane, side-to-side. The rotation may be on a vertical axis that extends through the bearing 146. The platform 142 may rotationally mount to the base 144 through the bearing 146 and thereon be rotatable over the base 144. In the illustrated embodiment, the platform 142 mounts to a platform mount 170 that includes a bearing mount 172 and a drive mount 174. A central portion of the platform 142 may attach to the bearing mount 172 using clamps or bolts or other attachment structures. The drive mount 174 may or may not attach to the platform 142 at a position outward of the bearing mount 172, which may include a position adjacent to a periphery edge or end of the platform 142. The drive mount 174 motion transfer arm 176 extends between the bearing mount 172 and a drive belt attachment member 178 to transfer motion provided by a drive module 180 to the platform 142 or bearing mount 172 in the illustrated configuration.

With particular reference to the views provided in FIGS. 12-15, the drive module 180 includes a motor bracket 182 to which a motor 184 (see FIG. 15) is mounted. The drive module 180 may attach to or be integral with the base 144. Torque generated by the motor 184 is applied to a motor shaft 186, the rotation of which is utilized to translate a drive belt 188. The drive module 180 may include one or more pulleys 190 (see, e.g., FIG. 14) configured to support translation of the drive belt 188 as it is driven by the motor shaft 186. The motor shaft 186 may comprise or operatively couple to a pulley 190. For example, in the illustrated embodiment, the motor shaft 186 connects to pulley 190d such that the pulley 190d rotates with the motor shaft 186.

While any suitable motor 184 may be used, the motor 184 is preferably selected to provide smooth, low noise operation with high torque at low rpm that may be precisely controlled for both position and speed. For example, the motor 184 may be a 3-phase permanent magnet synchronous motor (PMSM), a 3-phase brushless DC motor (BLDC), and the like which may be driven by sinusoidal currents. For controlling speed and position of the motor 184, a motor driver may synthesize three independent sinusoidal voltages with controllable frequency and amplitude for each phase. The synthesized voltages may have a constant phase offset of 120°, which reflects the position offset of three motor windings. The motor driver may comprise three half-bridges, one for each of the three phases, which generate three independent sinusoidal voltages. Each half-bridge may comprise two MOSFET transistors acting like low resistance electronic switches. By applying two mutually inverted pulse-width modulated (PWM) signals on those switches, the average voltage output from half-bridge may be set anywhere from 0 V to 12V DC. These voltages are connected to the motor terminals in order to create sinusoidal currents in windings of the motor 184 and appropriate magnetic flux in a motor stator.

The use of a BLDC motor is advantageous as it enables direct control of both amplitude and frequency without the need for an additional motor or additional gears to manipulate amplitude. The elimination of gears may enable quieter operation, which is an advantage in this application. It also reduces the number of moving mechanical parts, which may lead to an improvement in robustness. The use of a brushless motor may also extend the life of the motor by eliminating brush wear. Typical inductive motors have an optimum RPM and achieve lower speeds with gearing. Applications with continuous change of direction tend to be difficult for these motors. An advantage of the BLDC motor is that it operates well at a wide range of frequencies (RPMs) and has high torque at low RPMs, which facilitate the rapid change of direction needed by this application.

In order to achieve silent operation, the PWM frequency, the frequency at which the half-bridges are turned on and off, may be set above 20 kHz and preferably around 40 kHz. The PWM frequency is unrelated to the frequency at which the motor 184 rotates the platform 142. Required PWM signals for a driver stage may be generated by a microcontroller (MCU) based on a control algorithm. The control algorithm may determine the desired amplitude and frequency of motion based on input from an infant motion sensing device, an infant noise sensing device, an infant vital sign sensing device such as a sensor for heart rate, breathing, oxygenation and the like as discussed elsewhere herein and in U.S. patent application Ser. No. 15/055,077, filed Feb. 26, 2016. An open-loop control method which relies on the ability of the motor rotor to stay locked with the stator magnetic flux may be used such that control of the position and rotational speed of the motor shaft 186, may be achieved by control of the three winding currents alone.

The drive system 100 may include a controller operable to control movements of the platform 142. For example, the controller may include a control board 168 configured to control amplitude and frequency of the platform movements by modulating operation of the motor 184. The controller may include or communicate with a user interface to receive inputs and control instructions and/or output information regarding the operation of the system or an infant. The controller may be configured to collect data from one or more sensors and control output of motion and/or sound in response to the collected data. In various embodiments, the controller may be similar to that described in as described in U.S. patent application Ser. No. 14/448,679, filed Apr. 31, 2014, or U.S. patent application Ser. No. 15/055,077, filed Feb. 26, 2016. In some embodiments, the controller integrates with or be separate from the controller described above with respect to the weight detection system.

As introduced above, output of the motor 184 is transferred to drive belt 188, the translation of which further transfers the motor output to the platform 142 via coupling of the drive belt attachment member 178 to the drive belt 188. The drive belt attachment member 178 may couple to the belt 188 in any suitable manner. In the illustrated embodiment, the drive belt attachment member 178 attaches to the belt 188 via clamping to the drive belt 188.

The drive belt 188 may comprise a belt or chain. When a chain is used one or more pulleys 190 may include spaced apart teeth that insert within gaps between pins in the chain to assist in transferring power to the chain. In the illustrated embodiment, the drive belt 188 comprises a belt having teeth or ribs formed along a side thereof that engage between corresponding teeth or rib contours on one or more pulleys 190 that the drive belt 188 rotates when translated by the motor 184. In another embodiment, the drive belt 188 may include flat sides.

As introduced above, the drive module 180 may include one or more pulleys 190 that support the movement of the drive belt 188. While various arrangements of pulleys 190 may be used, in the illustrated embodiment the motor shaft 186 couples to a transfer belt 192 via pulley 190d. Translation of the transfer belt 192 is transmitted to a transfer pulley 190a to drive rotation of the same. Rotation of the transfer pulley 190a is translated to the drive belt 180, the translation of which is supported by the transfer pulley 190a and idler pulleys 190b, 190c. Thus, rotation of the motor shaft 186 translates transfer belt 192 to rotate the transfer pulley 190a. Rotation of the transfer pulley 190a translates drive belt 188, and translation of drive belt 188 rotates idler pulleys and imparts corresponding lateral movement at the drive belt attachment member 178. The lateral movement at the drive belt attachment member 178 levers the platform 142 or platform mount 170 on the bearing 146 to rotate the platform 142 over the base 144. Corresponding reversal of the motor 184 drives lateral movement of the drive belt attachment member 178 in the opposite direction to provide oscillating movement of the platform 142. The illustrated transfer pulley 190a includes a lower portion that couples to the transfer belt 192 and an upper portion that couples to the drive belt 188. In other embodiments, the transfer pulley 190a may couple to the transfer belt 192 along an upper portion and couple to the drive belt 188 along a lower portion. In various embodiments, additional belts and/or pulleys 190 may be used to modify location or direction of belt movements. The drive module 180 may optionally include a tensioner 194 that engages the drive belt 188 to allow adjustment of tension on drive belt 188.

While the platform 142 is shown mounted to the platform mount 170, it is to be appreciated that the platform 142 may mount to the base 144 through the bearing 146 without utilizing a bearing mount 172 and/or the platform 142 may attach to the drive module 180 directly in a manner similar to that described herein with respect to the drive mount 174. In some embodiments, the platform mount 170 may extend outwardly of the bearing mount 172 to attach to the platform 142 at other locations outward of the central portion of the platform 142, such as adjacent to a perimeter of the platform 142 for example. In some embodiments, the bearing mount 172 comprises one or more frame members that extend from the bearing mount 172 that attach to or otherwise provide support for the platform at peripheral locations beneath the platform 142.

In another embodiment, the motor output may be directly transmitted to the bearing mount 172. For example, a motor shaft 186 may mechanically or frictionally engage a side or edge of the bearing mount 172 to drive rotation on the bearing 146. In one example, the motor shaft includes teeth that engage corresponding teeth or gears associated with the bearing mount 172 to translate the torque generated by the motor to rotation of the platform 142. In another embodiment, the drive system 100 includes a linear motor that pushes and pulls the motion transfer arm 176 to rotate the platform 142.

In some embodiments, the drive system 100 described herein is utilized in a sleep device as described above with respect to FIG. 3. For example, a sleep device may include a weight detection system 1 including one or more weight sensors 2 and/or one or more additional sensors for measuring additional parameters may include drive system 100. In various embodiments, the drive system 100 is incorporated in an infant calming/sleep aid device as described in U.S. patent application Ser. No. 14/448,679, filed Apr. 31, 2014, or U.S. patent application Ser. No. 15/055,077, filed Feb. 26, 2016, and include a control system for determining a behavior state of the infant, e.g., motion detection, sound detection, and/or detection of other parameters, and initiating a response including rotation of the platform 142 in an oscillating manner to soothe or induce sleep. For example, the drive system 100 may drive oscillatory motion at 0.5-1.5 cycles per second (cps) of about 2" excursions, but if the baby is fussy the device responds by delivering a smaller excursion (e.g. <1.3") at a faster rate (about 2-4.5 cps). This fast and small motion may deliver the specific degree of rapid acceleration-deceleration force to the semicircular canals in the vestibular mechanism of the inner ear to activate the calming reflex. The reciprocating motion may have a maximum amplitude of less than 1.3 inches during the rapid phase of motion (~2-4.5 cps), further ensuring safety of the infant. In some embodiments, sound may also be output from speakers to soothe the infant. In one example, in response to detection of infant distress, both vigorous motion of the platform 142 and a loud sound can be provided. For example, providing motion of the platform 142 at a frequency greater than 0.5 Hz and an amplitude that is greater than 1 inch, along with sound having an intensity of at least 65 dB, may provide appropriate stimulation of the infant. Of course, other amounts of stimulation are also envisioned. In another or a further example, at a baseline, sound output may produce a low-pitch, rumbling sound at about 65 dB to about 74 dB. If the behavior state of the infant becomes more distressed, the a more high pitched audio track may be output. In a further example, the higher pitched audio track may be output at a louder volume of about 75 dB to about 95 dB.

Figure 16:
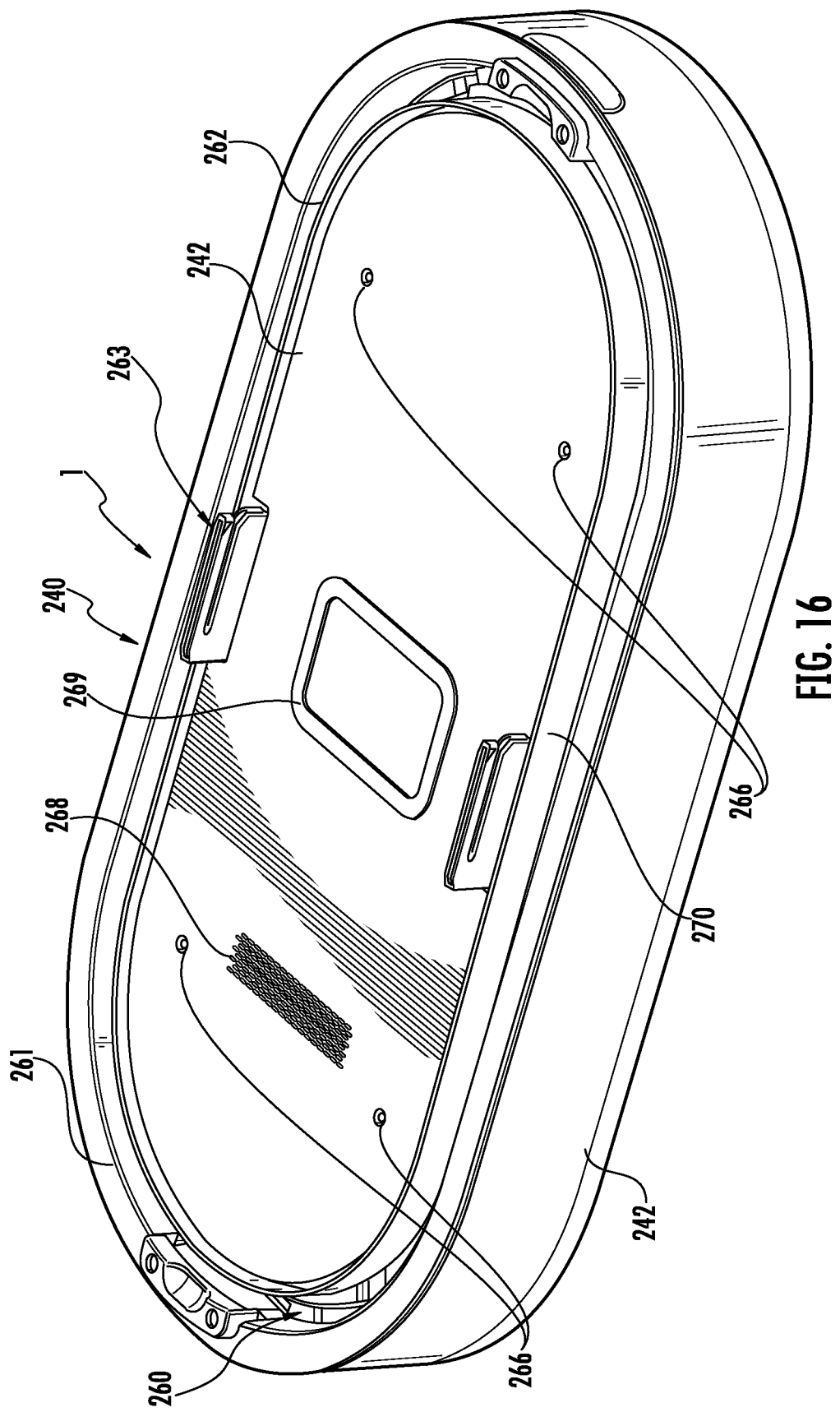
FIG. 16 is a perspective view of a configuration of a weight detection system for a sleep device according to various embodiments described herein.
Figure 17:
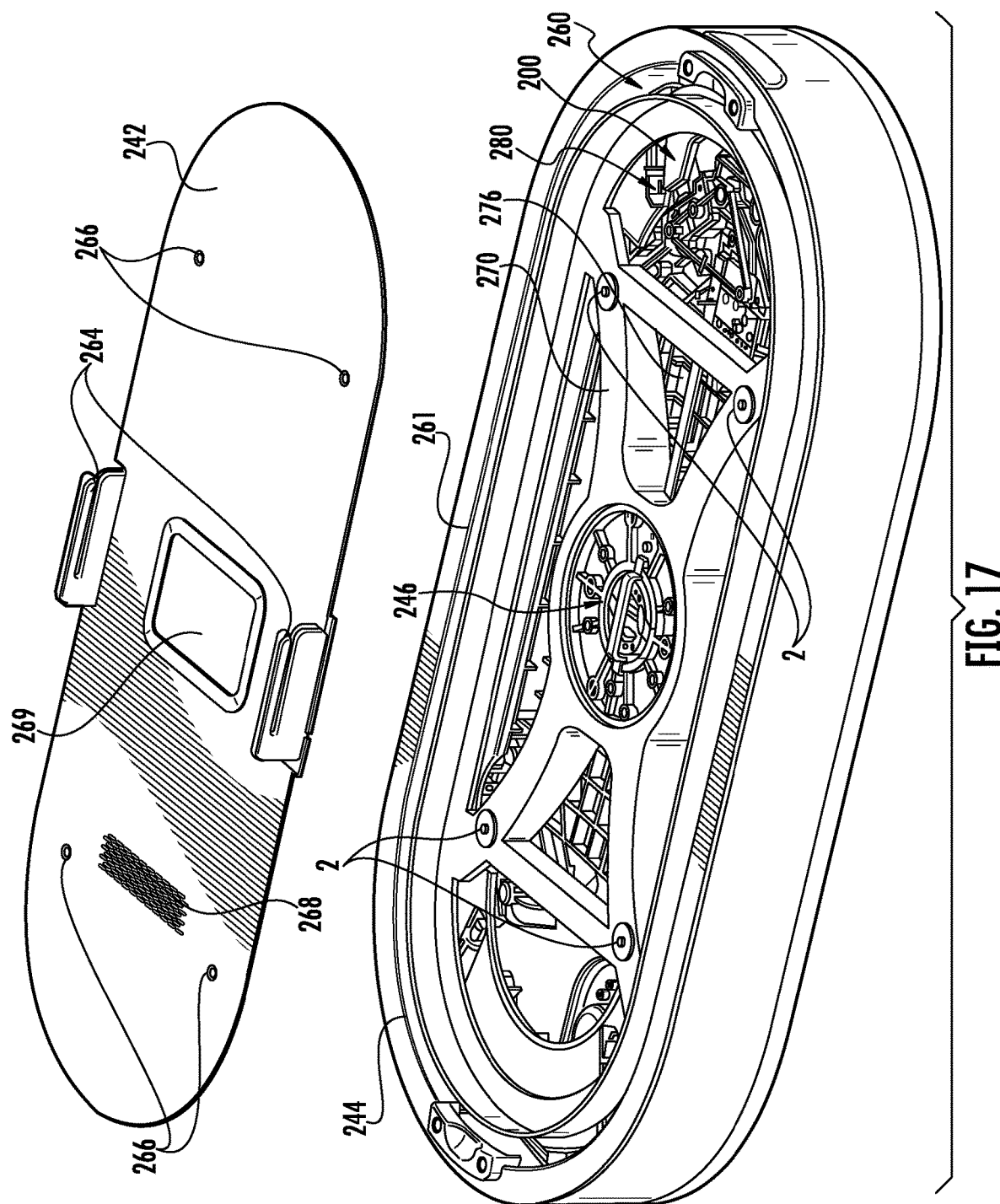
FIG. 17 illustrates an exploded view in perspective of the weight detection system for a sleep device show in FIG. 16 with the platform separated from the base according to various embodiments described herein.
Figure 18:
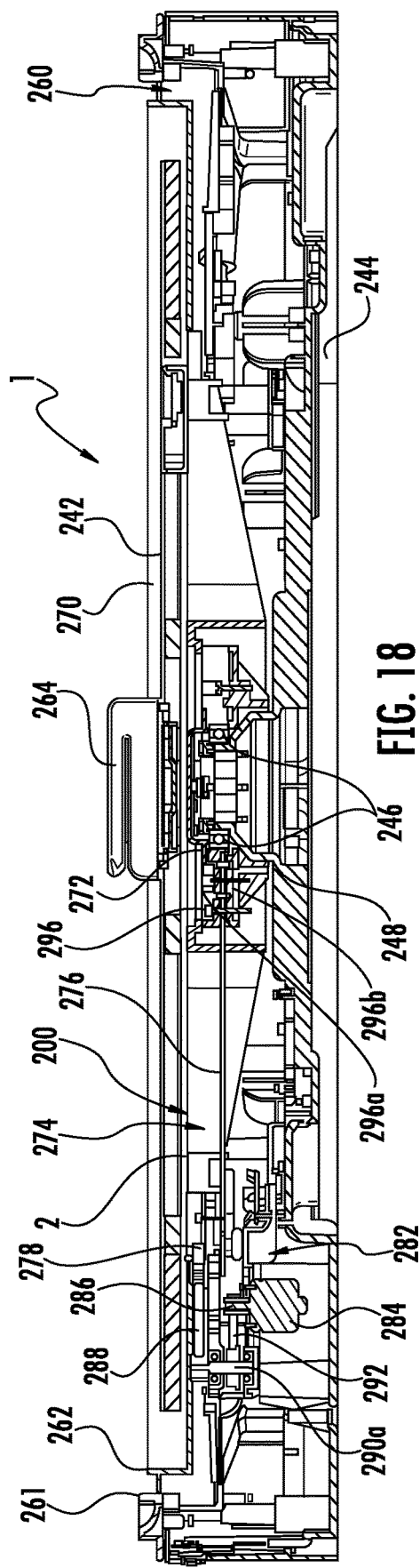
FIG. 18 is a longitudinal cross-section view of the weight detection system for a sleep device show in FIG. 16 according to various embodiments described herein.
Figure 19:
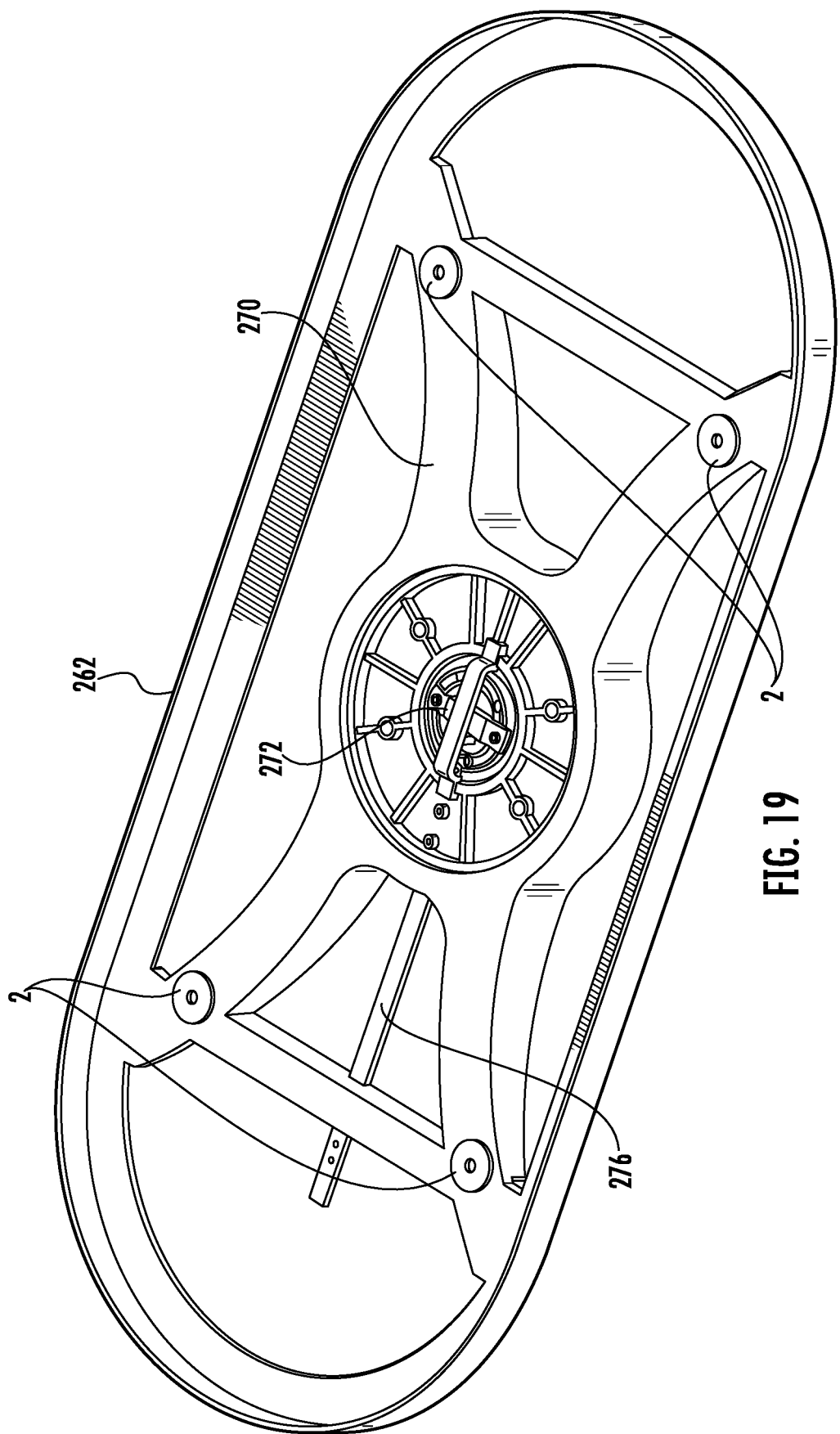
FIG. 19 is an isolated view in perspective of the platform mount depicted in FIG. 17 and FIG. 18 according to various embodiments described herein.
Figure 20:
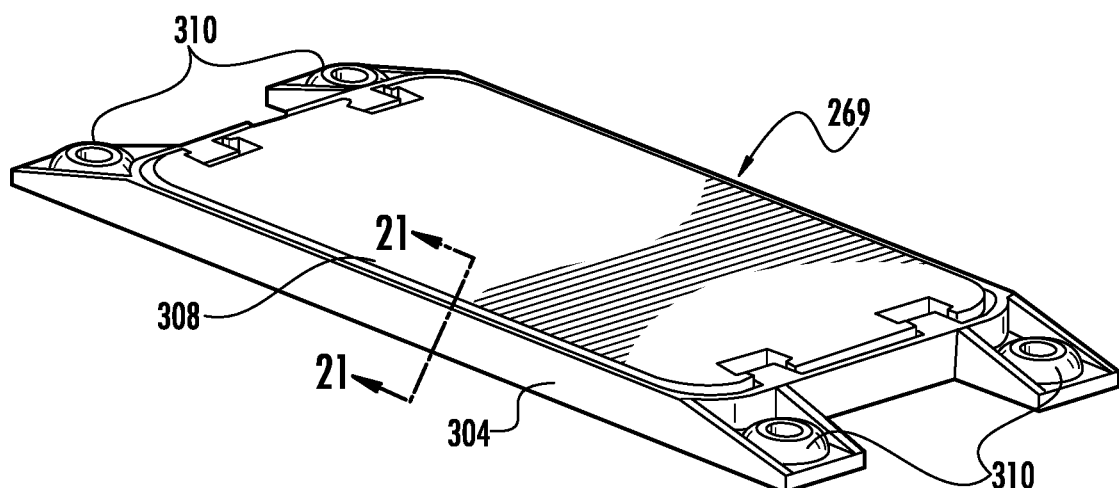
FIG. 20 is a perspective view of a breath sensor according to various embodiments described herein.
Figure 21:
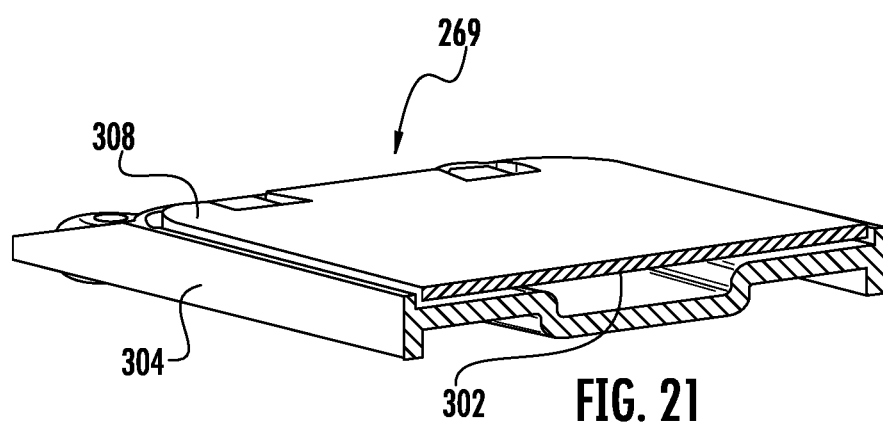
FIG. 21 is a cross-section view of the breath sensor shown in FIG. 20 taken along section 21 in FIG. 20 according to various embodiments described herein.
Figure 22:
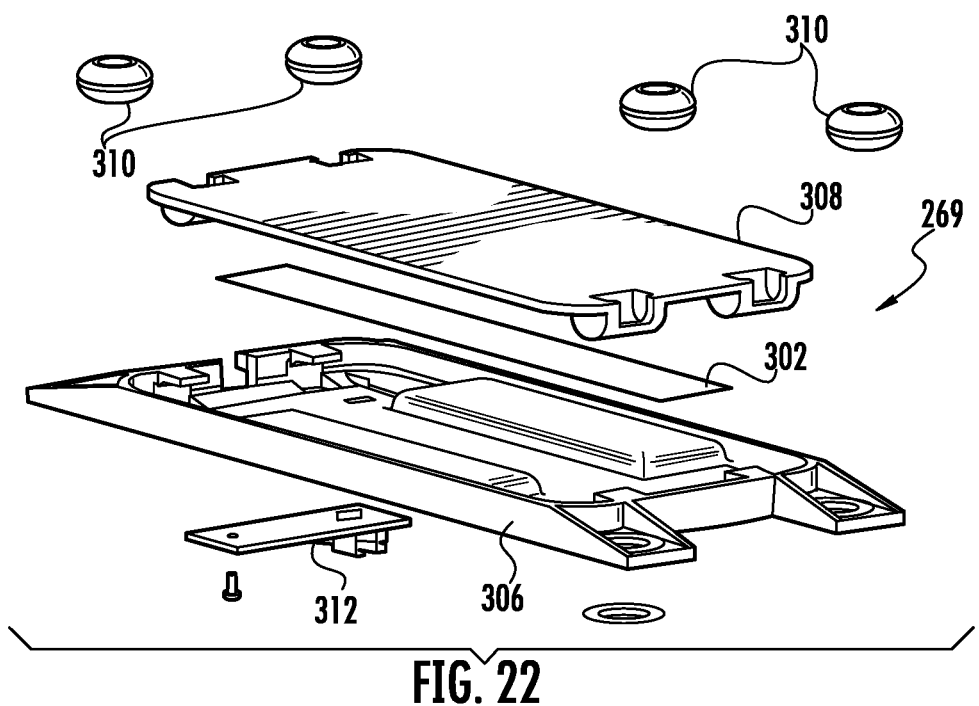
FIG. 22 is an exploded view of the breath sensor shown in FIG. 20 according to various embodiments described herein.
Figure 23:
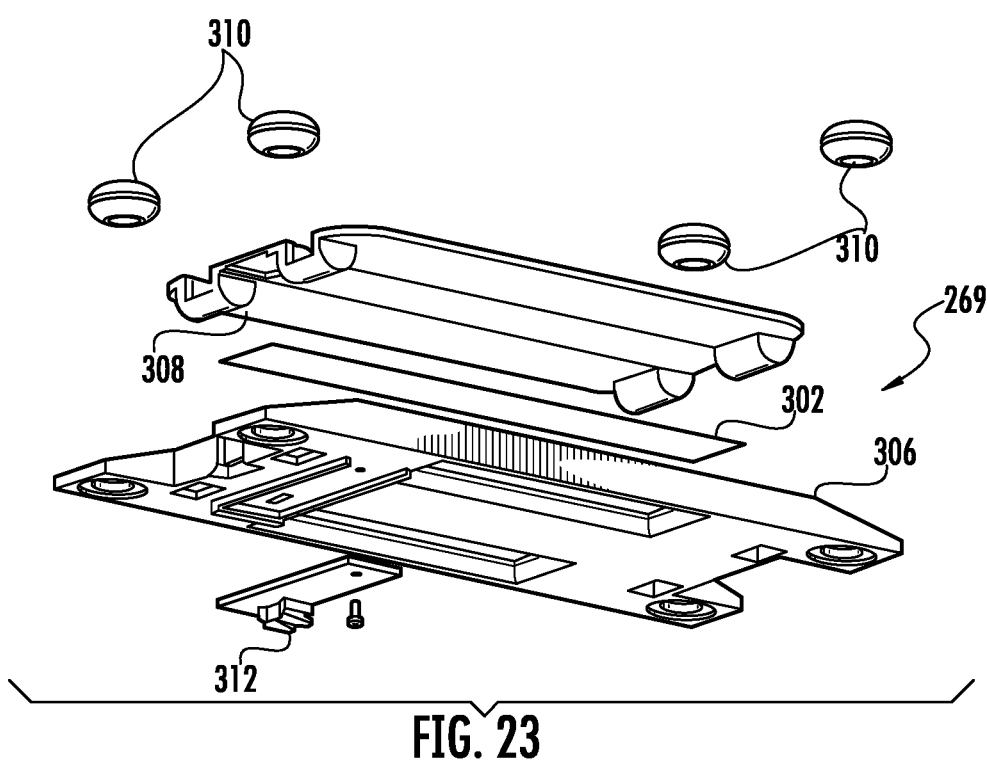
FIG. 23 is an exploded view of the breath sensor shown in FIG. 20 according to various embodiments described herein.

FIGS. 16-19 illustrate another configuration of a sleep device 240 incorporating the weight detection system 1. A base 244, platform 242, and related features are shown in FIGS. 16-18; however, various sleep device configurations may be used. For example, the sleep device 240 may have a configuration as described with respect to FIG. 2, 3, 10, or 11 and include a bassinet, for example.

The weight detection system 1 may include or be configured to operate in conjunction with a base 244, a platform 242, and one or more weight sensors 2. Weight sensors 2 may include load cells, strain gauges, compression sensors, or other weight sensor configurations.

The platform 242 couples to a platform mount 270 at one or more attachment points 266. In the illustrated example, the weight sensors 2 are positioned at attachment points 266 to locate between the platform 242 and platform mount 270. While other configurations may be used to position the weight sensor 2 between the platform 242 and platform mount 270, the one or more weight sensors 2 may include load cells or other weight sensor 2 configuration. Additionally or alternatively, weight sensors may include a gyro, strain gauge, piezo sensor, resistive potentiometer, accelerometer, or combinations thereof.

Weight sensors 2 may be configured to collect weight data in a manner as described with respect to FIG. 1. For example, the weight sensors 2 may be configured to measure weight of an infant positioned on the platform 242. The weight sensor 2 may be configured to collect weight data continuously, periodically, at predetermined intervals, upon receiving an instruction to collect weight data, and/or upon the occurrence of an event, such as when an infant is placed on the platform 242. In one embodiment, a user may define or schedule when weight measurements are to be taken or input an instruction via a user interface to collect weight data in a manner as described above. The platform 242 may be mounted to the platform mount 270 at the attachment points 266 such that the platform compresses against the weight sensors 2. In one embodiment, weight sensors 2 and/or a controller (see, e.g., FIG. 1) may calibrate weight sensors 2, e.g., upon startup to zero out the weight of the platform 242.

In the illustrated embodiment, the weight detection system 1 integrates with a sleep device 240 having a platform 242 configured to be movable above the base 242. For example, the platform 242 may be rotatable over a bearing base 248 fixed to the base 242, which may also include the bearing base 248. Rotation may be on a vertical axis that extends through a bearing 246 on which the platform 242 is rotatable relative to the base 244. In some embodiment, the platform 242 may be configured to move in other or additional motion patterns, such as any described herein. As depicted, the platform 242 mounts to a platform mount 270 that includes a bearing mount 272 for rotatably mounting over the base and a drive mount 274 for mounting to a drive system 200. A central portion of the platform 242 may attach to the bearing mount 272 using clamps or bolts or other attachment structures. As noted above, in the illustrated embodiment, the platform 242 mounts to the platform mount 271 at attachment points 266 through the weight sensors 2.

As introduced above, the sleep aid device including the weight detection system 1 includes a drive system 200 configured to selectively move the platform 242. The drive system 200 may be configured in a manner similar to that described above with respect to drive system 100 (see FIGS. 10-15) wherein similar features are identified by similar numbers. For example, the drive system 200 includes a drive module 280 comprising a motor 284 housed in a motor bracket 282. Motor output rotates a motor shaft 286 that drives corresponding rotation of transfer pulley 290a via a transfer belt 292. Rotation of transfer pulley 290a is translated to a drive belt 288, which is coupled to the platform 244 via the drive mount 274. The drive mount 274 includes a drive belt attachment member 278 comprising a clamp that clamps the drive belt 288 to couple to the movements of the drive belt 288. The drive belt attachment member 278 attaches to motion traction arm 176 or directly to the platform 242 or platform mount 270. The drive mount 274 in the illustrated embodiment includes a motion transfer arm 276 that extends between the bearing mount 272 and a drive belt attachment member 278 to transfer motion provided by a drive module 280 to the platform 242 and/or bearing mount 272. In the illustrated embodiment, the motion transfer arm 276 couples to the platform mount 270 and/or platform 242 at a transfer arm coupling 296. While other coupling configurations may be used, the transfer arm coupling 296 includes an upper clamp portion 296a and a lower clamp portion 296b configured to clamp the motion transfer arm 276 to couple the platform mount 270 to transfer arm 276. In another embodiment, the motion transfer arm 276 is retained by pins, bolts, or is integral with the platform mount 278 or platform. It should be appreciated that other configurations may be used to couple to the motion of the drive belt 288, e.g., the platform mount 270 or platform 242 may directly couple to the drive belt 288.

To provide room for the platform 242 to move, a gap region 260 may be provided between an interior facing side 261 of the base 244 and an outer side or rim 262 of the platform mount 270, although in other embodiments, the gap region 261 may be provided between the interior facing side 261 of the base 244 and an outer side of the platform 242. In the illustrated embodiment, the rim 262 extends upward to define an area to receive the platform 242 such that the platform 242 recesses below an upper extent of the rim 262. The rim 262 may assist in retaining a mattress (not shown) positioned on the platform 242 during motion of the platform 242. The raised rim 262 may also limit opportunities for the mattress to rest an edge onto the rim 262 to thereby receive a portion of a load of the mattress or infant positioned on the mattress.

As introduced above, the weight detection system 1 so arranged with the platform 242 and/or bearing mount 272 described with respect to FIGS. 16-19 may be incorporated in sleep devices 240 having different drive systems and/or configurations. In one embodiment, the weight detection system 1 is incorporated with respect to a platform in a manner described herein with respect to FIGS. 16-18 wherein the platform 242 is not configured to be moved by a drive system. For example, weight sensors 2 may be positioned between a platform 242 and a frame, such as the platform mount 270, and the platform 242 sleep device may not include a drive system. In another embodiment, the weight detection system 1 is incorporated with respect to a platform and drive system configured to move in another manner, e.g., up and down; a lateral, longitudinal, or diagonally directed wave motion; a rocking motion; lateral side-to-side motion on a horizontal plane; a head-to-toe motion on a plane on a horizontal plane; and/or a tilting motion on an axis of rotation that extends through or parallel to the major plane of the platform, such as laterally to tilt a first longitudinal end of the platform 242 upward while tilting a second longitudinal end downward or longitudinally to tilt a first lateral side of the platform upward while tilting a second lateral side downward. In one example, the rotation or tilt axis extends a long a horizontal plane through or relative to a central longitudinal or lateral division or bisection of the platform 242. Such motions may be selected based on data collected by sensors and analysis thereof as described herein.

In some embodiments, the weight detection system 1 described with respect to FIGS. 16-19 may include a controller and additional sensors as described above with respect to FIG. 1 and elsewhere herein. For example, the controller may include an analysis module and communicate with and provide outputs to a user interface and/or data storage device. The controller may also include or interface with another controller operable to control a motor that drives motion of the platform 242.

In one embodiment, drive system 200 may be incorporated in an infant calming/sleep aid device as described in U.S. patent application Ser. No. 14/448,679, filed Apr. 31, 2014, or U.S. patent application Ser. No. 15/055,077, filed Feb. 26, 2016, and include a control system for determining a behavior state of the infant, e.g., motion detection, sound detection, and/or detection of other parameters, and initiating a response including rotation of the platform 242 in an oscillating manner based on analysis of the measured data to soothe or induce sleep. For example, the drive system 200 may drive oscillatory motion at 0.5-1.5 cycles per second (cps) of about 2" excursions, but if the baby is fussy the device responds by delivering a smaller excursion (e.g. <1.3") at a faster rate (about 2-4.5 cps). This fast and small motion may deliver the specific degree of rapid acceleration-deceleration force to the semicircular canals in the vestibular mechanism of the inner ear to activate the calming reflex. The reciprocating motion may have a maximum amplitude of less than 1.3 inches during the rapid phase of motion (~2-4.5 cps), further ensuring safety of the infant. In some embodiments, sound may also be output from speakers to soothe the infant. In one example, in response to detection of infant distress, both vigorous motion of the platform 242 and a loud sound can be provided. For example, providing motion of the platform 242 at a frequency greater than 0.5 Hz and an amplitude that is greater than 1 inch, along with sound having an intensity of at least 65 dB, may provide appropriate stimulation of the infant. Of course, other amounts of stimulation are also envisioned. In another or a further example, at a baseline, sound output may produce a low-pitch, rumbling sound at about 65 dB to about 74 dB. If the behavior state of the infant becomes more distressed, the a more high pitched audio track may be output. In a further example, the higher pitched audio track may be output at a louder volume of about 75 dB to about 95 dB.

The platform 242 also includes an optional attachment mechanism 263 for attachment of a sleep sack configured to secure an infant to the platform in a manner described in U.S. patent application Ser. No. 14/448,679, filed Apr. 31, 2014, or U.S. patent application Ser. No. 15/055,077, filed Feb. 26, 2016. In the illustrated embodiment, the attachment mechanism 263 comprises two attachment members 264. The attachment members 264 include clips positioned at lateral sides of the platform 242. Attachment mechanism, such as those illustrated, may similarly be incorporated with the other embodiments of a platform of a sleep device described herein.

The sleep device 240 or weight detection system 1 may include one or more additional sensors for measuring additional parameters. Such sensors may be associated with a sensor system or control system such as described in U.S. patent application Ser. No. 14/448,679, filed Apr. 31, 2014, or U.S. patent application Ser. No. 15/055,077, filed Feb. 26, 2016, that includes the weight detection system 1 or integrates data collected from the weight detection system 1. In the illustrated embodiment, the platform 242 also incorporates one or more optional speakers 268 for outputting audio. The audio may comprise tracks selected by a control system or controller thereof based on inputs and/or analysis of infant cries, motions, or other data related to the infant collected by sensors positioned to detect parameters of the infant. The sensors may include one or more of a pressure sensor (e.g., pressure mat), video sensor (e.g., to detect movement and/or collect size data), or motion sensors. The sensors also include a breath sensor 269 configured to detect breathing, heartbeat, and/or motion. The breath sensor 269 may be a part of or configured to operably communicate with a controller as described herein and/or a breath detection module of a control system such as described in U.S. patent application Ser. No. 16/905,424, filed Jun. 18, 2020, which is incorporated herein by reference.

In one embodiment, the breath sensor 269 comprises one or more motion sensors comprising one or more piezo electric elements, load cells, gyros, strain gauges, resistive potentiometer, accelerometers or the like. It is to be appreciated that while the breath sensors 269 in the illustrated embodiments may be referred to as comprising or consisting of one or more piezo electric elements, such embodiments may also be configured for use with other motion sensors such as load cells, gyros, strain gauges, resistive potentiometer, accelerometers or the like. The sensors may be configured to detect pressure, force, strain, or acceleration changes, which may include vibrations. For example, piezo electric elements may detect propagation of sound waves or pressure changes through solid or gas resulting sensor vibrations transduced to a heartbeat detection module and/or breath detection module for analysis, which may include a controller or sensor control system as described herein. The sensors may include or communicate with a processor and/or storage medium storing analysis instructions executable by the processor for analysis of a signal generated by the sensors. In one embodiment, the processor is a component of the controller as described herein and/or breath detection module as described in U.S. patent application Ser. No. 16/905,424, filed Jun. 18, 2020. In one example, the sensors comprise one or more piezo electric strips. Such strip sensor configurations may be suspended in some implementations. Strip sensors may be attached to surfaces such that movement of the surfaces stresses or strains the sensor. Strip sensors may be positioned between two surfaces such that changes in forces transmitted between the two surfaces are detected by the sensor. Strip sensors may be position in a sealed gas volume or within a solid such that vibrations transmitted along surrounding material are detected by the sensor via changes in pressure. The strip sensors may be suspended to isolate the sensors from motion of a movable platform. A piezo electric element may be positioned at an appropriate location relative to and within an appropriate distance from the infant to detect motion of the infant, such as vertical motion or other directional motion and/or an associated pressure, force, or vibration. In one example, multiple piezo electric strip sensors may be used at various locations. In an embodiment, a piezo electric element of a breath sensor 249 may be positioned under a back or other location along the back of the infant when the infant is located on a platform. For example, the piezo electric element may be embedded in a mat, mattress, infant garment, sleep sack, or attached to a movement platform upon which the infant is placed. Motion sensors other than piezo electric elements may similarly be configured and utilized as describe above and elsewhere herein with respect to piezo electric elements.

FIGS. 20-24 illustrate various views of two additional embodiments of a breath sensor 269 for a sleep device. The exemplary breath sensors 269 include tray design configurations for attachment to a platform of a sleep device, but other design configurations may be used. The breath sensor 269 attaches to the platform and is positioned to underlay a mattress and an infant positioned thereon. The breath sensor 269 may be positioned within a recess and approximately flush or slightly above a plane defined by a surrounding upper surface of the platform. The breath sensors 269 may include a piezo electric element 302, which may be a strip or other configuration. Force, strain, or pressure, such as vibration, applied along the piezo electric element 302 may be converted to an electric signal for detection of breathing of an infant positioned on the platform. As noted above, the breath sensor 269 may also be used to detect heartbeat, motion, and other biological signals.

With particular reference to the embodiment shown in FIGS. 20-23, the piezo electric element 302 is housed within a sensor housing 304 having a base 306 and a cover 308. The base 306 may attach to a platform through one or more gromet 310 configured to dampen propagation of vibrations from the platform to the housing 304. The piezo electric element 302 may be positioned to detect force, strain, or pressure, such as vibration, from above the platform to generate an electric signal for detection of breathing of an infant positioned on the platform. A data signal port 312 electrically couples to the piezo electric element 302 to receive and transmit the electrical signal, wired or wirelessly, to a controller or sensor control system as described herein. The piezo electric element 302 may be suspended within the housing, attached to an upper wall of the cover (as shown), or positioned within a sealed portion of the housing 304 to detect pressure changes, force, or strain. The cover 308 may be constructed to allow for controlled deflection through half-moon or crescent shaped bumpers on extreme ends of the cover 308 and a limitation of vertical travel distance (to prevent overstretching the sensor 302) via controlled side walls.

Figure 24:
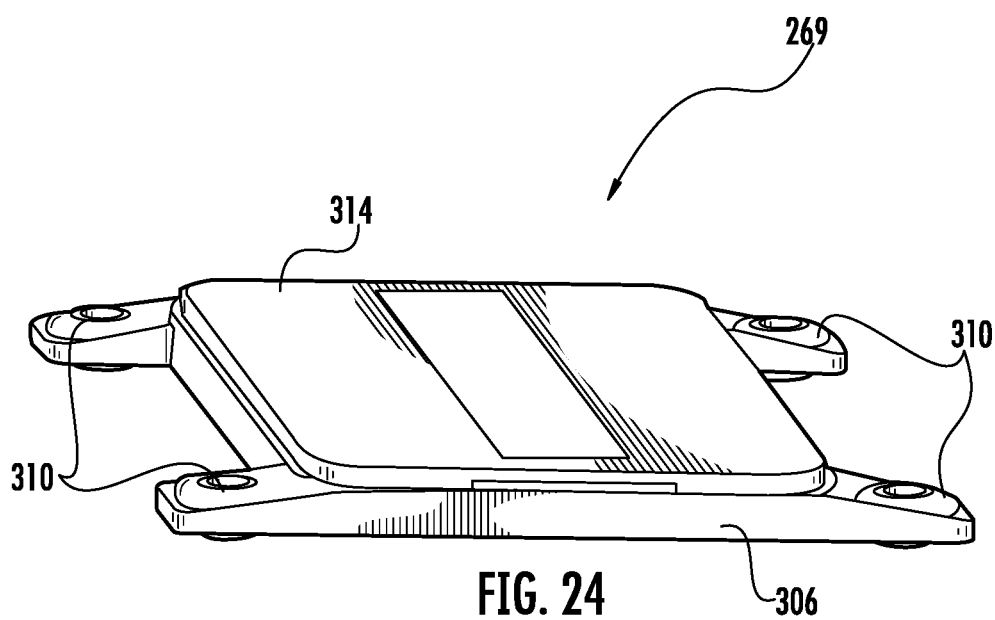
FIG. 24 is a perspective view of a breath sensor according to various embodiments described herein.

FIG. 24 illustrates another embodiment of the breath sensor 269 including a piezo electric element 302 positioned on a material configured to isolate the piezo electric element 302 from vibrations from a platform upon which it mounts. As shown, the piezo electric element 302 positions on a foam pad 314 that rests on a base 306. The foam pad 314 may extend to rest flush with the base 306 along its underside. In another embodiment, one or more cavities are positioned between the underside of the foam pad 314 and the base 306. In another embodiment, the piezo electric element 302 positions on a firm surface and one or more sides of the element 302 are surrounded positioned adjacent to the foam pad 314. The foam pad 314 may extend along sides of the piezo electric element 302 to damped vibrations propagated along a mattress the breath sensor 269 underlies to further focus detection to portions of the mattress above the piezo electric element 302. In one embodiment, the foam pad 314 is supported on a cover that covers the base 306. The base 306 may attach to the platform through one or more gromet 310 configured to dampen propagation of vibrations from the platform to the piezo electric element 302. The breath sensor 269 may include a data signal port 312, which may be similar to data signal port 312 described with respect to FIGS. 20-23, that electrically couples to the piezo electric element 302 to receive and transmit the electrical signal, wired or wirelessly, to a controller or sensor control system as described herein. In various embodiments, the breath sensor 249 may be utilized in a sleep device as described herein. In use, an infant may be positioned on a mattress resting on the platform of the sleep device in the conventional manner such that a height dimension of the infant extends along the longitudinal axis of the mattress. As noted above, the infant may be secured in position on the mattress relative to the platform with straps or clips within a sleep sack or other harnessing device.

Figure 27:
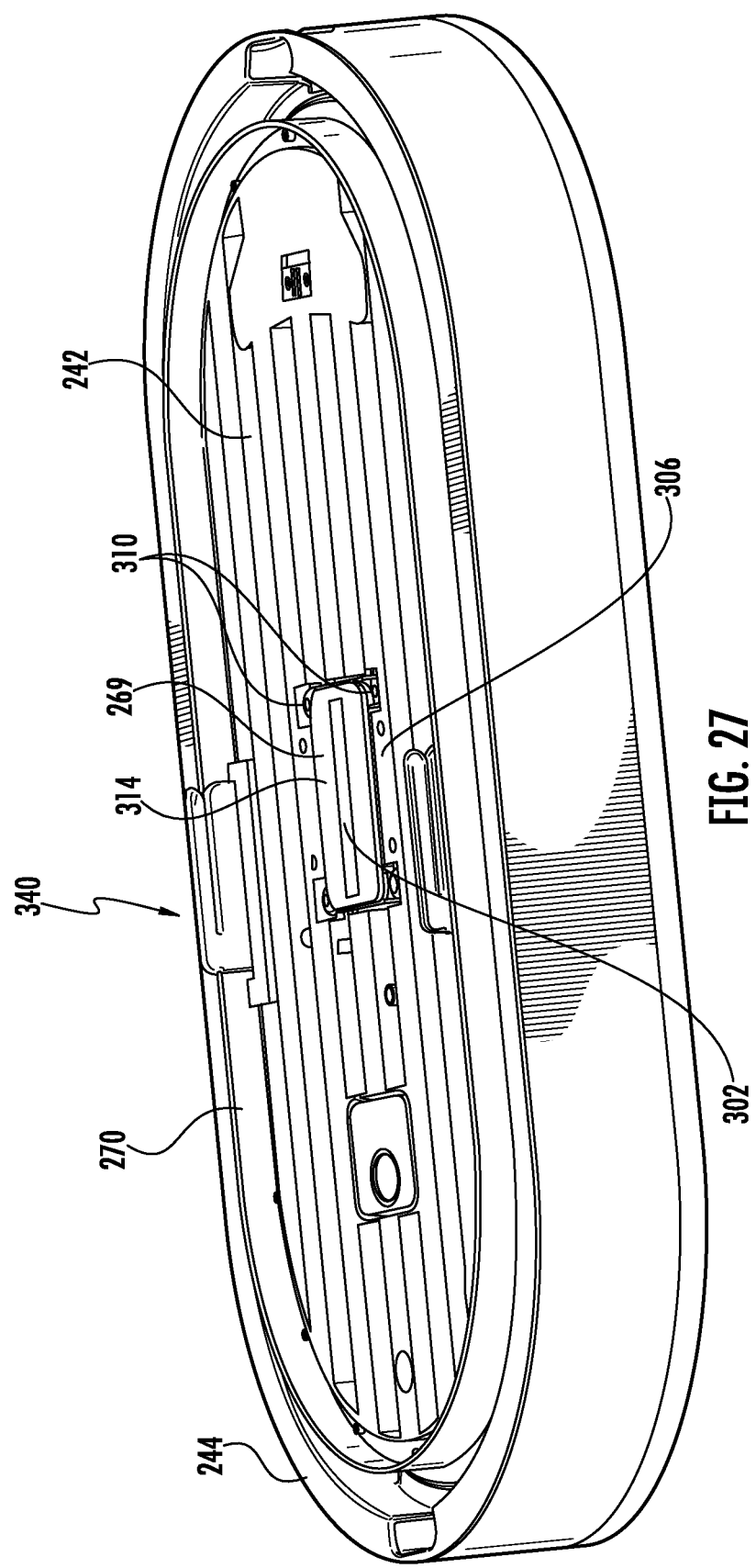
FIG. 27 is a perspective view of a base and platform of a sleep device including a breath sensor according to various embodiments described herein.

FIG. 27 shows an example of the base 244 and platform 242 of a sleep device 340 including a breath sensor 269 according to various embodiments described herein. The breath sensor 269 includes a piezo electric element 302 and base 306 similar to that described with respect to FIGS. 20-24. The piezo electric element 302 may be positioned on or between a foam pad 314 in a manner described above with respect to FIG. 24 and its variations. Gromets 310 may also be used to dampen vibrations. The sleep device 340 may be similar to sleep device 240 (FIG. 16) and be configured with a movable platform 249.

In the embodiment illustrated in FIG. 24, the piezo electric element 302 comprises a strip that extends laterally or transverse to the longitudinal expanse of a platform to correspondingly underlie a mattress or pad positioned on the platform. The embodiment illustrated in FIGS. 20-23, the piezo electric element 302 comprises a strip that extends longitudinally or about parallel to the longitudinal expanse of a platform to correspondingly underlie a mattress or pad positioned on the platform. Thus, a piezo electric element 302 comprising a strip may be configured to position under an infant on the platform, preferably beneath the torso transverse or corresponding to the height dimension of the infant. In one example, of the breath sensor 249 of FIG. 24, the piezo electric element 302 may be positioned at other angles. For example, FIG. 27 illustrates an example platform 242 and platform mount 270 supported by a base 244 wherein a breath sensor 269 is positioned thereon and includes a piezo electric element 302 that extends longitudinally along the longitudinal axis of the platform 242. The platform 244 may be configured to move as described herein. The configuration shown in FIG. 27 may also include a drive system and/or a weight detection system as also described herein. In some examples of the breath sensor 249 of FIGS. 20-23, the piezo electric element 302 may be positioned transversely or at other angles. As noted above, in some embodiments, other breath sensor configurations may be used.

Figure 25:
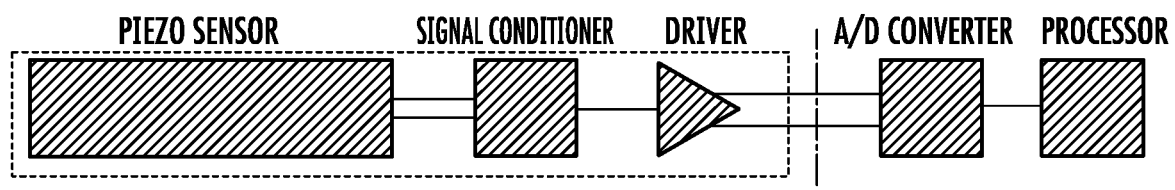
FIG. 25 schematically illustrates a process flow for detecting breathing according to various embodiments.

FIG. 25 schematically illustrates a process flow for detecting breathing using a breath sensor 279, such as breath sensor 269, including a piezo electric element according to various embodiments. In one example, the breath sensor 279 may be similar to breath sensor 269 that described with respect to FIGS. 20-24 and 27. Force, strain, or pressure applied along the piezo electric element of the breath sensor 279 may be converted to an electric signal that may be conditioned by a signal conditioner 281. The conditioned signal may be transmitted through a driver 283 to an analog digital convertor 285 to convert to a digital signal, which may then be processed by a processor. The processor may be a component of a controller or sensor control system as described herein or may be configured to transmit processed data to the same.

Figure 26:
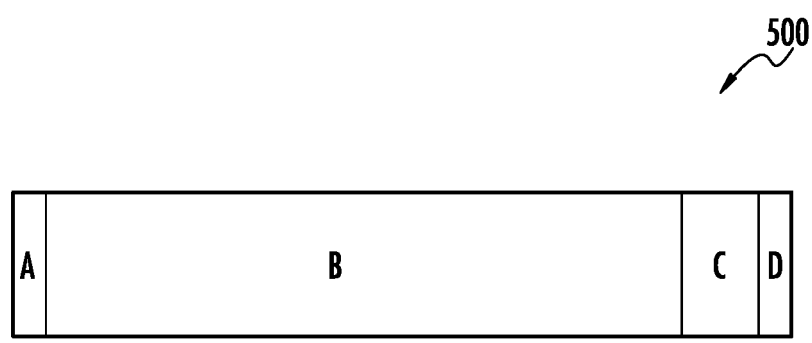
FIG. 26 schematically illustrates an example buffer for use by a breath detection module with respect to detection of intermittent breathing and breath per minute analysis according to various embodiments described herein.

FIG. 26 schematically illustrates an example buffer 500 for use by a breath detection module with respect to detection of intermittent breathing and breath per minute analysis according to various embodiments. The buffer 500 may be utilized by a breath detection module employing a breath sensor device as described herein. For example, the breath detection module may utilize a piezo approach using a signal from a breath sensor comprising a piezo sensor that is placed such that when the baby is breathing the sensor is pressed, strained, or vibrated and thus generates a signal. In one example, the breath sensor may be placed under a mattress. The generated signal may then be filtered and analyzed. In one embodiment, filtering may include amplification and/or conversion. For example, the signal may propagate to an amplifier and then an analog to digital converter. The breath detection module may then read the amplified values at a sample rate of 100 Hz, but those having skill in the art will appreciate upon reading the present disclosure that other sampling rates may be used.

The buffer 500 may store data according to a first in first out (FIFO) order. Portion A represents sample which is removed from the buffer 500 when a new sample arrives. Portion D illustrates new acquired sample at the sample rate. Portion C represents a portion of the buffer that together with portion D is used as a buffer length of a predetermined period for detection of intermittent breathing. Portion B represents a portion of the buffer that together with portions A, C, and D comprise the buffer length of a predetermined period use for breaths per period calculation.

The illustrations of arrangements described herein are intended to provide a general understanding of the structure of various embodiments, and they are not intended to serve as a complete description of all the elements and features of the systems, modules, and processes that might make use of the structures described herein. While the present disclosure generally describes the weight detection system and process with respect to a bassinet having a moveable platform, movable bassinets are but only one of many potential applications. Indeed, those having skill in the art will appreciate that the weight detection system and processes described herein may find application in many infant apparatuses, such as bouncy chairs, car seats, or other infant apparatuses in which an infant may sleep and that may include significant non-weight related motion and/or sounds. Other arrangements may be utilized and derived therefrom, such that structural and logical substitutions and changes may be made without departing from the scope of this disclosure.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity. Any numerical range recited herein includes all values and ranges from the lower value to the upper value. These are only examples of what is specifically intended, and all possible combinations of numerical values and ranges between and including the lowest value and the highest value enumerated are to be considered to be expressly stated in this application. Numbers modified by the term "approximately" or "about" are intended to include +/−10% of the number modified.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

What is claimed is:

1. An infant sleep device, the sleep device comprising:
a platform for supporting an infant;
a base upon which the platform is supported, wherein the platform is configured to move above and relative to the base;
one or more weight sensors positioned to measure weight of an infant positioned on the platform; and
a controller configured to receive weight data collected by the one or more weight sensors, wherein the controller includes an analysis module configured to analyze the weight data, and wherein the analysis module is configured to compare collected weight data to previously collected weight data to determine if the infant is underfed, overfed, or properly fed and/or satiated.

2. The sleep device of claim 1, wherein the one or more weight sensors are positioned between the platform and the base.

3. The sleep device of claim 2, wherein the one or more weight sensors comprise one or more load cells.

4. The sleep device of claim 2, wherein the one or more weight sensors comprise at least one of a strain gauge, piezo sensor, resistive potentiometer, accelerometer, or gyro.

5. The sleep device of claim 1, further comprising a platform mount that mounts between the base and the platform and is configured to move above and relative to the base with the platform, wherein the platform couples to the platform mount, wherein the one or more weight sensors are positioned between the platform mount and the platform.

6. The sleep device of claim 5, wherein the one or more weight sensors comprise or more of a load cell, strain gauge, gyro, or accelerometer.

7. The sleep device of claim 5, further comprising one or more bearings positioned between the platform mount and the base, wherein the platform mount mounts onto the bearing and is movable over and relative to the base thereon, and wherein the sleep device further comprises a drive system operable to drive the movement of the platform mount and coupled platform over and relative to base on the one or more bearings.

8. The sleep device of claim 1, wherein the analysis module is configured to determine a feeding state of the infant, track weight of the infant over time, generate a weight profile, identify rapid weight gain or weight loss, identify abnormal weight change patterns, identify movements and restlessness of the infant, or combination thereof.

9. The sleep device of claim 1, wherein the analysis module is configured to track presence of an infant on the platform, and wherein the controller is configured to transmit a notification to a user interface when the analysis module determines absence of the infant on the platform.

10. The sleep device of claim 1, wherein the analysis module is configured analyze the weight data to track infant restlessness and/or physical distress, and wherein the controller is configured to take an action when the analysis module determines at least one of infant restlessness or physical distress, wherein the action is selected from generating a jolting movement of the platform or transmitting a notification to a user interface.

11. The sleep device of claim 1, wherein the controller is configured to transmit collected weight data to a back-end system for analysis and/or historical storage, wherein the analysis of the weight data includes one or more of identification of population trends and/or individual historical trends; comparative analysis of weight data associated to an individual infant versus population; or comparative analysis of the collected data associated with the infant versus population.

12. The sleep device of claim 1, wherein the analysis module utilizes momentary fluctuations in weight data to identify movement of an infant on the platform.

13. The sleep device of claim 12, wherein the analysis module is configured to analyze the weight data associated with movement to identify restlessness and/or physical distress.

14. The sleep device of claim 12, wherein the analysis module is configured to analyze the weight data associated with movement and sound data collected by one or more sound sensors to identify a choke event.

15. A weight detection system for a sleep device, the system comprising a controller configured to receive weight data collected by one or more weight sensors positioned to detect a weight of an infant supported on a platform of a sleep device, wherein the controller includes an analysis module configured to analyze the weight data collected by the one or more weight sensors, and wherein the analysis module is configured to determine a feeding state of the infant, track weight of the infant over time, generate a weight profile, identify rapid weight gain or weight loss, identify abnormal weight change patterns, identify movements and restlessness of the infant, or combination thereof.

16. The system of claim 15, wherein the analysis module is configured to track changes in weight over time.

17. The system of claim 15, wherein the analysis module is configured to track presence of an infant on the platform and to transmit a notification to a user interface when the presence of the infant is not detected on the platform.

18. The system of claim 15, wherein the controller is configured to transmit collected weight data to a back-end system for analysis and/or historical storage, wherein the analysis of the weight data includes one or more of: identification of population trends and/or individual historical trends; comparative analysis of weight data associated to an individual infant versus population; or comparative analysis of the collected data associated with the infant versus population.

19. The sleep device of claim 15, wherein the analysis module utilizes momentary fluctuations in weight data to identify movement of an infant on the platform.

20. The sleep device of claim 19, wherein the analysis module is configured to analyze the weight data associated with movement to identify restlessness and/or physical distress.

21. The sleep device of claim 19, wherein the analysis module is configured to analyze the weight data associated with movement and sound data collected by one or more sound sensors to identify a choke event.

22. A weight detection system for a sleep device, the system comprising a controller configured to receive weight data collected by one or more weight sensors positioned to detect a weight of an infant supported on a platform of a sleep device, wherein the controller includes an analysis module configured to analyze the weight data collected by the one or more weight sensors, and wherein the analysis module is configured to track duration of time the infant spends on the platform of the sleep device.

23. A weight detection system for a sleep device, the system comprising a controller configured to receive weight data collected by one or more weight sensors positioned to detect a weight of an infant supported on a platform of a sleep device, wherein the controller includes an analysis module configured to analyze the weight data collected by the one or more weight sensors, and wherein the analysis module is configured to identify feeding patterns and how the feeding patterns affect sleep timing, duration, or quality.

24. A weight detection system for a sleep device, the system comprising a controller configured to receive weight data collected by one or more weight sensors positioned to detect a weight of an infant supported on a platform of a sleep device, wherein the controller includes an analysis module configured to analyze the weight data collected by the one or more weight sensors, and wherein, when the analysis module determines the infant is underfed, the controller is configured to generate a notification to a user interface that infant is underfed.

25. A weight detection system for a sleep device, the system comprising a controller configured to receive weight data collected by one or more weight sensors positioned to detect a weight of an infant supported on a platform of a sleep device, wherein the controller includes an analysis module configured to analyze the weight data collected by the one or more weight sensors, wherein, when the analysis module is configured to generate a feeding schedule based on a desired or optimal sleep time, and wherein the feeding schedule identifies a time range and amount of food the infant is to be fed within the time range prior to the desired or optimal sleep time.

26. The system of claim 25, wherein the sleep time includes a sleep duration.

27. A weight detection system for a sleep device, the system comprising a controller configured to receive weight data collected by one or more weight sensors positioned to detect a weight of an infant supported on a platform of a sleep device, wherein the controller includes an analysis module configured to analyze the weight data collected by the one or more weight sensors, wherein the controller is configured to receive data related to the infant from one or more additional sensors, wherein the analysis module is configured to analyze the data collected from the one or more additional sensors to determine a behavior state of the infant and correlate the behavior state to weight data collected proximate to the collection of the data collected from the one or more additional sensors to identify how weight patterns affect behavior state, and wherein the one or more additional sensors comprise one or more of motion sensors, sound sensors, breath sensors, biological sensors, or combination thereof.

28. A weight detection system for a sleep device, the system comprising a controller configured to receive weight data collected by one or more weight sensors positioned to detect a weight of an infant supported on a platform of a sleep device, wherein the controller includes an analysis module configured to analyze the weight data collected by the one or more weight sensors, wherein the controller is configured to receive data from one or more additional sensors configured to collect length and/or circumference data with respect to the infant, and wherein the one or more additional sensors comprise a pressure mat.

29. A method comprising: measuring weight of an infant positioned on a platform of a sleep device with one or more weight sensors positioned to measure loads placed on the platform; transmitting the measured weight data to an analysis module; analyzing the measured weight data with the analysis module, wherein analyzing comprises comparing the measured weight data to previously measured weight data and determining a feeding state of the infant; and outputting an indication of the feeding state to a user interface.

* * * * *